(12) United States Patent
Sindrey et al.

(10) Patent No.: US 7,491,691 B2
(45) Date of Patent: Feb. 17, 2009

(54) CONNECTIVE TISSUE STIMULATING PEPTIDES

(76) Inventors: Dennis R. Sindrey, 524 Marlatt Dr., Oakville, Ontario (CA) L6H 5X3; Sydney M. Pugh, 499 Maple Lawn Dr., Glenburnie, Ontario (CA) K0H 1S0; Timothy J. N. Smith, 47 Copperfield Dr., Kingston, Ontario (CA) K7M 1M3

( * ) Notice: Subject to any disclaimer, the term of this patent is extended or adjusted under 35 U.S.C. 154(b) by 0 days.

(21) Appl. No.: 10/513,202

(22) PCT Filed: May 2, 2003

(86) PCT No.: PCT/CA03/00634

§ 371 (c)(1), (2), (4) Date: Jul. 5, 2005

(87) PCT Pub. No.: WO03/093314

PCT Pub. Date: Nov. 13, 2003

(65) Prior Publication Data

US 2005/0288229 A1 Dec. 29, 2005

Related U.S. Application Data

(60) Provisional application No. 60/377,271, filed on May 3, 2002.

(51) Int. Cl.
*A61K 38/00* (2006.01)
(52) U.S. Cl. .............................. 514/2; 514/13; 514/14; 514/15; 514/16; 514/17; 530/326; 530/327; 530/328; 530/329; 530/330; 424/57
(58) Field of Classification Search ........................ None
See application file for complete search history.

(56) References Cited

U.S. PATENT DOCUMENTS

| | | | |
|---|---|---|---|
| 4,235,871 A | 11/1980 | Papahadjopoulos et al. | |
| 4,761,471 A | 8/1988 | Urist ........................... 530/350 | |
| 4,762,915 A | 8/1988 | Kung et al. | |
| 5,013,649 A | 5/1991 | Wang et al. ................. 435/69.1 | |
| 5,100,874 A * | 3/1992 | Odake et al. .................. 514/18 | |
| 5,106,748 A | 4/1992 | Wozney et al. ............ 435/252.3 | |
| 5,141,905 A | 8/1992 | Rosen et al. ................ 435/69.1 | |
| 5,169,837 A | 12/1992 | Lagarde et al. ................. 514/21 | |
| 5,187,076 A | 2/1993 | Wozney et al. ............. 435/69.1 | |
| 5,403,825 A | 4/1995 | Lagarde et al. ................. 514/21 | |
| 5,599,792 A | 2/1997 | Kronis et al. ................. 514/12 | |
| 5,646,134 A * | 7/1997 | Yates ........................... 514/108 |
| 5,958,428 A | 9/1999 | Bhatnagar ................... 424/400 |
| 5,965,136 A | 10/1999 | Baylink | |
| 5,972,623 A | 10/1999 | Krane et al. | |
| 6,030,792 A | 2/2000 | Otterness et al. | |
| 6,060,255 A | 5/2000 | Shibuya et al. | |
| 6,187,076 B1 | 2/2001 | Sugahara et al. | |
| 6,287,816 B1 | 9/2001 | Rosen et al. ................ 435/69.4 |
| 6,323,146 B1 | 11/2001 | Pugh et al. | |
| 6,333,312 B1 | 12/2001 | Kuberasampath et al. | |
| 6,344,439 B1 | 2/2002 | Kitamura et al. ............... 514/2 |
| 6,352,973 B1 | 3/2002 | Tam ........................... 514/12 |

FOREIGN PATENT DOCUMENTS

| | | | |
|---|---|---|---|
| EP | 0992586 A2 | * | 10/1999 |
| JP | 50046656 | * | 4/1975 |
| WO | WO-90-11366 | | 10/1990 |
| WO | WO 91/18098 | * | 11/1991 |
| WO | WO-92-03125 | | 3/1992 |
| WO | WO-93/07889 | * | 4/1993 |
| WO | WO-93-20859 | | 10/1993 |
| WO | WO 94/26893 | | 11/1994 |
| WO | WO-98-12222 | | 3/1998 |
| WO | WO-98-40406 | | 9/1998 |
| WO | WO-02-07748 | | 1/2002 |

OTHER PUBLICATIONS

[Retreived from] http://web.archive.org/web/20010405155813/http://www.biospecifics.com/collagendefined.html, 2001, 2 pages {retreived on Mar. 12, 2007].*
[Retreived from] "http://web.archive.org/web/20010412200503/http://www.lab.anhb.uwa.edu.au/mb140/CorePages/Connective/Connect.htm" 2001, 10 pages, [Retreived on Mar. 9, 2007].*
[Retreived from] http://web.archive.org/web/20020606150054, 2002. 2 pages [retreived on Mar. 12, 2007].*
Nachman et al., Pseudodoipeptide analogs of the pyrokinin/PBAN (FXPRLa) insect neuropeptide family containing carbocyclic Pro-mimetic conformational components, Regulatory Peptides, 1995, 359-370, 57.

* cited by examiner

*Primary Examiner*—Andrew D Kosar
*Assistant Examiner*—Satyanarayana R Gudibande
(74) *Attorney, Agent, or Firm*—Pandiscio & Pandiscio

(57) ABSTRACT

Novel peptides are described which comprise an amino acid motif selected from the group consisting of "PG", "GP", "PI" and "IG" and having up to 10 amino acids upstream and/or downstream of the amino acid motif, wherein "P" in the motif is proline or hydroxyproline and the peptide stimulates the development, maintenance and repair of bone, cartilage and associated connective tissue. The invention further relates to pharmaceutical compositions of these peptides, as well as therapeutic and prophylactic uses of such peptides.

33 Claims, 14 Drawing Sheets

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 1

Asn Gly Leu Pro Gly Pro Ile Gly Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Asn Gly Leu Pro Gly Pro Ile Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 3

Asn Gly Leu Xaa Gly Pro Ile Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
```

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Asn Gly Leu Xaa Gly Pro Ile Gly Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Asn Gly Leu Pro Gly Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Leu Pro Gly Pro
1

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Pro Gly Pro Ile Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Asn Gly Leu Pro Gly Pro Ile Gly Pro
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Pro Gly Pro Ile Gly Pro
1               5

<210> SEQ ID NO 10
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 10

Pro Gly Pro Ile Gly Pro Pro Gly Pro Arg
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Gly Pro Ile Gly
1

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Pro Gly Pro Ile Gly Pro Pro Gly Pro Arg Gly Arg Thr Gly Asp Ala
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Gly Pro Arg Gly Arg Thr Gly Asp Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Pro Gly Pro Ile Gly Pro Pro
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Pro Gly Pro Ile Gly Xaa
1               5
```

```
<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Pro Gly Pro Ile
1

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Gly Leu Pro Gly Pro Ile Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 18

Gly Pro Ile Gly Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Gly Pro Ile Gly Pro
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic

<400> SEQUENCE: 20

Pro Ile Gly Pro
1
```

CONNECTIVE TISSUE STIMULATING PEPTIDES

This is a U.S. national entry of International Application No. PCT/CA03/00634, filed on May 2, 2003, which claims benefit of U.S. Provisional Application No. 60/377,271, filed on May 3, 2002.

FIELD OF THE INVENTION

The present invention relates to the development, maintenance and repair of connective tissue. More specifically, the invention relates to the identification of novel peptides that are capable of influencing the formation and repair of skeletal tissues which include bone, cartilage and related connective tissues. The invention further relates to pharmaceutical compositions of these peptides, as well as therapeutic and prophylactic uses of such peptides.

BACKGROUND OF THE INVENTION

Throughout this application, various references are cited in parentheses to describe more fully the state of the art to which this invention pertains. The disclosure of these references are hereby incorporated by reference into the present disclosure.

Various agents have been identified and characterized for use in the stimulation of bone and/or cartilage formation and tissue repair. Examples of such agents may include for example, calcium preparations (e.g. calcium carbonate), calcitonin preparations, sex hormones (e.g. estrogen, estradiol), prostaglandin A1, bisphosphonic acids, ipriflavones, fluorine compounds (e.g. sodium fluoride), vitamin K, bone morphogenetic proteins (BMPs), fibroblast growth factor (FGF), platelet-derived growth factor (PDGF), transforming growth factor (TGF-$\beta$), insulin-like growth factors 1 and 2 (IGF-1, IGF-2), parathyroid hormone (PTH), epidermal growth factor (EGF), leukemia inhibitory factor (LIF), osteogenin, and bone resorption repressors such as estrogens, calcitonin and biphosphonates.

U.S. Pat. Nos. 5,169,837 and 5,403,825 disclose an osteogenic factor and method of extraction from crude extracts of mammalian bone. The osteogenic factor is capable of inducing bone growth as determined using a rat bone growth assay. U.S. Pat. No. 5,599,792 discloses parathyroid hormone (PTH) variants that exhibit bone stimulating activity and reduced vasoactivity.

Various patents disclose bone morphogenetic proteins (BMPs) and methods of isolating such proteins. BMPs are useful for the treatment of bone and cartilage defects. U.S. Pat. No. 4,761,471 discloses a method for purifying a mixed BMP composition from demineralized bone tissue; U.S. Pat. No. 5,013,649 discloses bone morphogenetic protein-3 (BMP-3); U.S. Pat. No. 5,106,748 discloses bone morphogenetic protein-5 (BMP-5); U.S. Pat. No. 6,187,076 discloses bone morphogenetic protein-6 (BMP-6); U.S. Pat. No. 5,141,905 discloses bone morphogenetic protein-7 (BMP-7); PCT Publication No. WO91/18098 discloses bone morphogenetic protein-8 (BMP-8); U.S. Pat. No. 6,287,816 discloses bone morphogenetic protein-9 (BMP-9); and PCT Publication No. WO94/26893 discloses bone morphogenetic protein-10 (BMP-10).

U.S. Pat. No. 6,352,973 discloses bone stimulating factor polypeptides for use in the treatment of bone disease. U.S. Pat. No. 6,344,439 discloses agents for promoting bone formation, the agents comprise the RGD binding sequence. U.S. Pat. No. 5,958,428 discloses synthetic compounds that promote cell binding with collagen.

While the aforementioned agents do have general use in aspects of bone repair, they also have various shortcomings. For example, some of the agents are relatively non-specific and thus not very effective at promoting bone tissue repair. Certain agents such as extracted factors are associated with the risk of immunogenicity, infection and/or disease transmission. Extraction from crude extracts of tissue or preparation via recombinant methods are also costly thus compromising commercial viability. Furthermore, some agents have secondary undesirable systemic or local effects. Most notable is the fact that several of the known agents may cause ectopic bone formation. Such abnormal bone formation is highly undesirable and may lead to serious medical complications.

There is therefore a need to provide novel peptides that have specific in vitro, in vivo, or ex vivo use for effectively influencing development, maintenance and repair of connective tissues.

SUMMARY OF THE INVENTION

The present invention provides a number of novel peptides and analogues thereof which are influential in skeletal biology in that the peptides serve to stimulate the normal formation of bone, cartilage and related connective tissues in vitro, in vivo, ex vivo and for tissue engineering applications. The functional analogues of these novel peptides contain one or more amino acid additions, substitutions or deletions to the disclosed peptide sequences.

The novel peptides herein described are generically referred to as BCSP ("<u>b</u>one and <u>c</u>artilage <u>s</u>timulating <u>p</u>eptides").

The invention also relates to nucleic acids encoding the isolated connective tissue promoting peptides and analogues thereof, expression vectors containing the nucleic acid molecules, host cells containing the nucleic acid molecules, compositions of such peptides and nucleic acids encoding therefor and antibodies to those peptides.

The novel peptides and nucleic acids encoding therefor can be used in compositions administered using a variety of carriers and methods to promote the formation and function of various connective tissues such as bone and cartilage. As such, the peptides and analogues thereof can be used to treat a variety of skeletal abnormalities which include but not limited to bone and cartilage defects due to trauma and/or disease.

The peptides and functional analogues thereof can be used in a variety of in vitro, in vivo or ex vivo applications and methods. Furthermore, the peptides and functional analogues thereof also have use in a variety of tissue engineering applications.

In one embodiment, the present invention provides therapeutic compositions and methods for the treatment of disorders involving abnormal bone and/or cartilage formation and associated abnormal skeletal development resulting from disease, arthritis and degenerative joint diseases involving cartilage degeneration. The therapeutic compositions and methods can also be used for the treatment of trauma induced skeletal or cartilage damage.

According to an aspect of the invention is a peptide comprising an amino acid motif selected from the group consisting of "PG", "GP", "PI" and "IG" and having up to 10 amino acids upstream and/or downstream of said amino acid motif, wherein "P" in the motif is proline or hydroxyproline, the peptide stimulating the development, maintenance and repair of bone, cartilage and associated connective tissue.

According to another aspect of the invention is a peptide comprising one or more "GP" and/or "PG" motifs and comprising up to a total of about 20 amino acids, wherein "P" in the motif is proline or hydroxyproline and the peptide induces the activity of bone and cartilage cells such that bone and cartilage tissue is developed, maintained and/or repaired.

The peptides of the invention stimulate the activity of bone cells, bone cell precursors and cells sharing lineage therewith. Similarly, the peptides of the invention stimulate the activity of cartilage cells, cartilage cell precursors and cells sharing lineage therewith. As such, these peptides have use in the stimulation of the formation of bone and cartilage as used in vitro, ex vivo and/or in vivo.

The peptide of the invention can be as few as three amino acids in length and more preferably, at least four amino acids in length. The peptide can further comprise one or more linkers, calcium binding motifs and agents and used for local or systemic applications.

According to another aspect of the invention, there is provided a peptide having a formula selected from the group consisting of:

X—(P$_1$)$_m$Gly(P$_2$)$_n$,   (I)

(P$_1$)$_m$Gly(P$_2$)$_n$-Z,   (II)

and

X—(P$_1$)$_m$Gly(P$_2$)$_n$-Z;   (III)

wherein P$_1$ and P$_2$ are selected from the group consisting of proline and hydroxyproline, m=0 or 1, n=0 or 1, where m and n are independently selected;

wherein X is selected from the group consisting of leucine, glycine-leucine, proline-isoleucine, glycine-proline-isoleucine, asparagine-glycine-leucine and proline-glycine-proline-isoleucine-glycine-proline; and wherein Z is selected from the group consisting of isoleucine, arginine, isoleucine-glycine, isoleucine-glycine-proline, isoleucine-glycine-hydroxyproline, isoleucine-glycine-proline-proline, isoleucine-glycine-proline-proline-glycine, isoleucine-glycine-proline-proline-glycine-proline, isoleucine-glycine-proline-proline-glycine-proline-arginine, isoleucine-glycine-proline-proline-glycine-proline-arginine-glycine-arginine-threonine-glycine-aspartate-alanine and arginine-glycine-arginine-threonine-glycine-aspartate-alanine.

Accordingly, in an aspect of the invention there are provided peptides having the following amino acid sequences and designated BCSP1 which has the amino acid sequence NGLPGPIGP* (SEQ. ID. NO. 1); BCSP2 which has the amino acid sequence NGLPGPIG (SEQ. ID. NO. 2); BCSP3 which has the amino acid sequence NGLP*GPIG (SEQ. ID. NO. 3); BCSP4 which has the amino acid sequence NGLP*GPIGP* (SEQ. ID. NO. 4); BCSP5 which has the amino acid sequence NGLPGP (SEQ ID. NO. 5); BCSP6 which has the amino acid sequence LPGP (SEQ. ID. NO. 6); BCSP7 which has the amino acid sequence PGPIG (SEQ ID. NO. 7); BCSP8 which has the amino acid sequence NGLPGPIGP (SEQ. ID. NO. 8); BCSP9 which has the amino acid sequence PGPIGP (SEQ ID. NO. 9); BCSP10 which has the amino acid sequence PGPIGPPGPR (SEQ. ID. NO. 10); BCSP11 which has the amino acid sequence GPIG (SEQ. ID. NO. 11); BCSP12 which has the amino acid sequence PGPIGPPGPRGRTGDA (SEQ. ID. NO. 12); BCSP13 which has the amino acid sequence GPRGRTGDA (SEQ. ID. NO. 13); BCSP14 which has the amino acid sequence PGPIGP (SEQ. ID. NO. 14); BCSP15 which has the amino acid sequence PGPIGP* (SEQ. ID. NO. 15); BCSP16 which has the amino acid sequence PGPI (SEQ. ID. NO. 16); BCSP17 which has the amino acid sequence GLPGPIG (SEQ. ID. NO. 17); BCSP18 which has the amino acid sequence GPIGP* (SEQ. ID. NO. 18); BCSP19 which has the amino acid sequence GPIGP (SEQ. ID. NO. 19); and BCSP20 which has the amino acid sequence PIGP (SEQ. ID. NO. 20). As used herein, P* is used to identify hydroxyproline. Each of these peptides can be used to elicit a connective tissue promoting response in vitro, in vivo and ex vivo.

In another aspect, the invention provides functional analogues of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 for eliciting a connective tissue promoting response in vitro, in vivo and ex vivo.

In another aspect, the invention provides mimetic analogues of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 for eliciting a connective tissue promoting response in vitro, in vivo and ex vivo.

In a further aspect of the invention, there are provided compositions for stimulating a connective tissue response in a mammal, for example, a human, said compositions comprising an effective amount of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 as well as functional analogues thereof and/or functional mimetics thereof together with a pharmaceutically acceptable diluent or carrier. Such compositions may be formulated to contain additional adjuvant(s), co-stimulatory molecules and/or stabilizers.

In accordance with another embodiment of the present invention is a composition for the stimulation of the development, maintenance and repair of bone, cartilage and related connective tissues, the composition comprising a peptide having a formula selected from the group consisting of:

X—(P$_1$)$_m$Gly(P$_2$)$_n$,   (I)

(P$_1$)$_m$Gly(P$_2$)$_n$-Z,   (II)

and

X—(P$_1$)$_m$Gly(P$_2$)$_n$-Z;   (III)

wherein P$_1$ and P$_2$ are selected from the group consisting of proline and hydroxyproline, m=0 or 1, n=0 or 1, where m and n are independently selected;

wherein X is selected from the group consisting of leucine, glycine-leucine, proline-isoleucine, glycine-proline-isoleucine, asparagine-glycine-leucine and proline-glycine-proline-isoleucine-glycine-proline;

wherein Z is selected from the group consisting of isoleucine, arginine, isoleucine-glycine, isoleucine-glycine-proline, isoleucine-glycine-hydroxyproline, isoleucine-glycine-proline-proline, isoleucine-glycine-proline-proline-glycine, isoleucine-glycine-proline-proline-glycine-proline, isoleucine-glycine-proline-proline-glycine-proline-arginine, isoleucine-glycine-proline-proline-glycine-proline-arginine-glycine-arginine-threonine-glycine-aspartate-alanine, arginine-glycine-arginine-threonine-glycine-aspartate-alanine; and a pharmaceutically acceptable carrier.

In accordance with another aspect of the present invention is a method for stimulating the development, maintenance and repair of bone, cartilage and associated connective tissue in a mammal, the method comprising administering an effective amount of a peptide comprising an amino acid motif selected from the group consisting of "PG", "GP", "PI" and "IG" and having up to 10 amino acids upstream and/or downstream of said amino acid motif, wherein "P" in the motif is proline or hydroxyproline.

In accordance with a further embodiment of the present invention is a therapeutic method for promoting connective tissue formation in a mammal which comprises administering to a mammal a peptide having a formula selected from the group consisting of:

$$X—(P_1)_m Gly(P_2)_n, \quad (I)$$

$$(P_1)_m Gly(P_2)_n\text{-}Z, \quad (II)$$

and $$X—(P_1)_m Gly(P_2)_n\text{-}Z; \quad (III)$$

wherein $P_1$ and $P_2$ are selected from the group consisting of proline and hydroxyproline, m=0 or 1, n=0 or 1, where m and n are independently selected;

wherein X is selected from the group consisting of leucine, glycine-leucine, proline-isoleucine, glycine-proline-isoleucine, asparagine-glycine-leucine and proline-glycine-proline-isoleucine-glycine-proline;

wherein Z is selected from the group consisting of isoleucine, arginine, isoleucine-glycine, isoleucine-glycine-proline, isoleucine-glycine-hydroxyproline, isoleucine-glycine-proline-proline, isoleucine-glycine-proline-proline-glycine, isoleucine-glycine-proline-proline-glycine-proline, isoleucine-glycine-proline-proline-glycine-proline-arginine, isoleucine-glycine-proline-proline-glycine-proline-arginine-glycine-arginine-threonine-glycine-aspartate-alanine and arginine-glycine-arginine-threonine-glycine-aspartate-alanine;

or a functional analogue or variant of (I), (II) and/or (III).

In accordance with still a further embodiment of the invention is a therapeutic method for promoting connective tissue formation in a subject, said method comprising administering to said subject one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 as well as functional analogues thereof.

In accordance with a further embodiment, the invention provides a method for treating damaged bone, cartilage and related tissue in a subject, comprising administering to the subject an effective amount of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof and/or mimetic analogues thereof wherein the peptide(s) stimulate connective tissue repair and formation.

In accordance with a further embodiment, the invention provides a method for enhancing osseous integration of orthopedic or dental implants in a subject comprising administering to the subject an effective amount of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof.

According to a further embodiment of the invention, there is provided a method of producing cartilage at a cartilage defect site in vivo, the method comprising:

implanting into the defect site a population of chondrogenic cells which have been cultured in vitro in the presence of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof.

The present invention encompasses methods of promoting cartilage repair at a cartilage defect site in vivo wherein de novo cartilage prepared by tissue engineering techniques in the presence of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof, has been implanted into the defect site.

According to another embodiment of the invention, there is provided a method for treating a degenerative joint disease characterized by cartilage degeneration, the method comprising:

delivering a therapeutically effective amount of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof to a disease site.

In accordance with a further embodiment, the invention provides a method for treating bone associated disorders in a mammal, comprising administering to the mammal's cells selected from the group consisting of osteoblastic cells, pre-osteoblastic cells, chondrocytes, pre-chondrocytes, skeletal progenitor cells derived from bone, bone marrow or blood, and mixtures thereof, treated with an effective amount of one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof.

The methods of the invention may involve providing systemic and/or local administration of the selected peptide(s) or functional analogues of the invention.

According to another aspect of the invention, there is provided a morphogenetic device for implantation at a bone site in a vertebrate, the device comprising:

an implantable biocompatible carrier; and one or more of the peptides selected from the group consisting of BCSP1, BCSP2, BCSP3, BCSP4, BCSP5, BCSP6, BCSP7, BCSP8, BCSP9, BCSP10, BCSP11, BCSP12, BCSP13, BCSP14, BCSP15, BCSP16, BCSP17, BCSP18, BCSP19 and BCSP20 and functional analogues thereof provided or dispersed within or on said carrier.

According to another aspect of the invention is a method for stimulation of bone development in a mammal, said method comprising administering an effective amount of one or more peptides selected from the group consisting of SEQ. ID. NO. 1, SEQ. ID. NO. 4, SEQ. ID. NO. 7, SEQ. ID. NO. 8, SEQ. ID. NO. 9, SEQ. ID. NO. 10, SEQ. ID. NO. 12, SEQ. ID. NO. 15 and SEQ. ID. NO. 18 as well as functional analogues and mimetic analogues thereof.

According to yet another aspect of the invention is a method for stimulation of cartilage development in a mammal, said method comprising administering an effective amount of one or more peptides selected from the group consisting of SEQ. ID. NO. 1, SEQ. ID. NO. 4, SEQ. ID. NO. 7, SEQ. ID. NO. 8, SEQ. ID. NO. 9, SEQ. ID. NO. 10, SEQ. ID. NO. 11 as well as functional analogues and mimetic analogues thereof.

According to yet another aspect of the invention is a method for screening for a peptide that stimulates bone and/or cartilage formation and associated connective tissue, said method comprising the steps of:

(a) contacting a first biological sample capable of undergoing bone and/or cartilage formation with a test peptide;

(b) separately contacting a second biological sample capable of undergoing bone and/or cartilage formation with a biologically effective amount of a peptide selected from the group consisting of NGLPGPIGP* (SEQ. ID. NO. 1); NGLPGPIG (SEQ. ID. NO. 2); NGLP*GPIG (SEQ. ID. NO. 3); NGLP*GPIGP* (SEQ. ID. NO. 4); NGLPGP (SEQ ID. NO. 5); LPGP (SEQ. ID. NO. 6); PGPIG (SEQ ID. NO. 7); NGLPGPIGP (SEQ. ID. NO. 8); PGPIGP (SEQ ID. NO. 9); PGPIGPPGPR (SEQ. ID. NO. 10); GPIG (SEQ. ID. NO. 11); PGPIGPPGPRGRTGDA (SEQ. ID. NO. 12); GPRGRTGDA (SEQ. ID. NO. 13); PGPIGPP (SEQ. ID. NO. 14); PGPIGP* (SEQ. ID. NO. 15); PGPI (SEQ. ID. NO. 16); GLPGPIG (SEQ. ID. NO. 17); GPIGP* (SEQ. ID. NO. 18); GPIGP (SEQ. ID. NO. 19); and PIGP (SEQ. ID. NO. 20) thereby providing a control;

(c) assessing the level of bone and/or cartilage formation resulting from step (a) and from step (b); and (d) comparing the levels of bone and/or cartilage formation assessed in step (c), whereby a peptide capable of stimulating bone and/or cartilage formation is identified by its ability to alter the level of bone and/or cartilage formation when compared to the control of step (b).

According to still another aspect of the invention is a method for screening for a modulator that stimulates bone and/or cartilage formation and associated connective tissue, said method comprising the steps of:

(a) contacting a first biological sample capable of undergoing bone and/or cartilage formation with a test compound and a biologically effective amount of a peptide selected from the group consisting of NGLPGPIGP* (SEQ. ID. NO. 1); NGLPGPIG (SEQ. ID. NO. 2); NGLP*GPIG (SEQ. ID. NO. 3); NGLP*GPIGP* (SEQ. ID. NO. 4); NGLPGP (SEQ ID.NO. 5); LPGP (SEQ. ID. NO. 6); PGPIG (SEQ ID. NO. 7); NGLPGPIGP (SEQ. ID. NO. 8); PGPIGP (SEQ ID. NO. 9); PGPIGPPGPR (SEQ. ID. NO. 10); GPIG (SEQ. ID. NO. 11); PGPIGPPGPRGRTGDA (SEQ. ID. NO. 12); GPRGRTGDA (SEQ. ID. NO. 13); PGPIGPP (SEQ. ID. NO. 14); PGPIGP* (SEQ. ID. NO. 15); PGPI (SEQ. ID. NO. 16); GLPGPIG (SEQ. ID. NO. 17); GPIGP* (SEQ. ID. NO. 18); GPIGP (SEQ. ID. NO. 19); and PIGP (SEQ. ID. NO. 20);

(b) separately contacting a second biological sample with a biologically effective amount of a peptide selected from the group consisting of NGLPGPIGP* (SEQ. ID. NO. 1); NGLPGPIG (SEQ. ID. NO. 2); NGLP*GPIG (SEQ. ID. NO. 3); NGLP*GPIGP* (SEQ. ID. NO. 4); NGLPGP (SEQ ID. NO. 5); LPGP (SEQ. ID. NO. 6); PGPIG (SEQ ID. NO. 7); NGLPGPIGP (SEQ. ID. NO. 8); PGPIGP (SEQ ID. NO. 9); PGPIGPPGPR (SEQ. ID. NO. 10); GPIG (SEQ. ID. NO. 11); PGPIGPPGPRGRTGDA (SEQ. ID. NO. 12); GPRGRTGDA (SEQ. ID. NO. 13); PGPIGPP (SEQ. ID. NO. 14); PGPIGP* (SEQ. ID. NO. 15); PGPI (SEQ. ID. NO. 16); GLPGPIG (SEQ. ID. NO. 17); GPIGP* (SEQ. ID. NO. 18); GPIGP (SEQ. ID. NO. 19); and PIGP (SEQ. ID. NO. 20) thereby providing a control;

(c) assessing the level of bone and/or cartilage formation resulting from step (a) and from step (b); and (d) comparing the levels of bone and/or cartilage formation assessed in step (c), whereby a modulator of bone and/or cartilage formation is identified by its ability to alter the level of bone and/or cartilage formation when compared to the control of step (b).

According to yet another aspect of the invention is a method for identifying peptides that stimulate the development, maintenance and repair of bone, cartilage and associated connective tissue, said method comprising:

determining whether said peptide has comparable activity to one or more of the peptides selected from the group consisting of NGLPGPIGP* (SEQ. ID. NO. 1); NGLPGPIG (SEQ. ID. NO. 2); NGLP*GPIG (SEQ. ID. NO. 3); NGLP*GPIGP* (SEQ. ID. NO. 4); NGLPGP (SEQ ID. NO. 5); LPGP (SEQ. ID. NO. 6); PGPIG (SEQ ID. NO. 7); NGLPGPIGP (SEQ. ID. NO. 8); PGPIGP (SEQ ID. NO. 9); PGPIGPPGPR (SEQ. ID. NO. 10); GPIG (SEQ. ID. NO. 11); PGPIGPPGPRGRTGDA (SEQ. ID. NO. 12); GPRGRTGDA (SEQ. ID. NO. 13); PGPIGPP (SEQ. ID. NO. 14); PGPIGP* (SEQ. ID. NO. 15); PGPI (SEQ. ID. NO. 16); GLPGPIG (SEQ. ID. NO. 17); GPIGP* (SEQ. ID. NO. 18); GPIGP (SEQ. ID. NO. 19); and PIGP (SEQ. ID. NO. 20);

wherein the activity is assessed by the analysis of one or more criteria selected from the group consisting of bone mineral density, bone mineral content, alkaline phosphatase activity, proliferation of osteoblasts, bone nodule formation, bone nodule mineralization, chondrocyte proliferation, collagen assay and proteoglycan assay.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE PREFERRED EMBODIMENTS

Figure 1:
FIG. 1 shows a histological section of a bone defect treated with a Skelite™/BCSP1 implant.

The present invention provides novel peptides and functional analogues thereof which are influential in the development, maintenance and repair of connective tissue both in vitro and in vivo in mammals and in ex-vivo tissue engineering. Such peptides have a variety of uses in connective tissue repair and regeneration.

The term "connective tissue" as used herein encompasses bone, cartilage and related connective tissues which are formed by cells sharing such lineage. Such cells may include for example osteoblasts, pre-osteoblasts, chondrocytes, pre-chondrocytes, and skeletal progenitor cells derived from bone, bone marrow or blood. As such, the peptides are useful for the development, maintenance and repair of normal structure of bones, cartilage and associated connective tissues.

"Bone" as used herein is known by those of skill in the art to be defined as the dense, semi-rigid, porous, calcified connective tissue forming the major portion of the skeleton of most vertebrates. It consists of a dense organic matrix an inorganic, mineral component, and cells contained therein.

"Cartilage" as used herein is known to those of skill in the art to be the tough, elastic, fibrous connective tissue found in various parts of the body, such as the joints, outer ear, and larynx. Cartilage is not calcified like bone but is produced by chondrocytes which share lineage with bone-forming osteoblasts.

"Related connective tissue" as used herein is defined as tissue which is related to bone and cartilage such as for example bone marrow and cells contained therein, tendons and ligaments.

In one embodiment, the peptides of the invention provide a "bone stimulating response" that leads to increased endochondral bone formation, increased bone mineralization, increased bone mineral density, increased bone mineral content and increased bone repair. In general this relates to positive effects on bone-forming cells including but not limited to osteoblasts, pre-osteoblasts, chondrocytes, and pre-chondrocytes leading to the production and secretion of increased amounts of mineralized matrix which is the basis for new bone tissue formation. The response is specific such that local delivery of the peptide(s) does not lead to ectopic bone formation.

As used herein, the phrase "BCSP" is meant to designate the novel "<u>b</u>one and <u>c</u>artilage <u>s</u>timulating <u>p</u>eptide". It will be appreciated by one of ordinary skill in the art that the BCSP peptides of the invention may be of a variable length being as little as three contiguous amino acids and more preferably at least 4 contiguous amino acids. In certain embodiments of the invention, the BCSP peptides of the invention comprise as little as 3 amino acids to as many as 10 or 20 amino acids or more. The peptide sequences as described herein utilize the standard 1-letter code for amino acids as is understood by one of skill in the art (Short Protocols In Molecular Biology, Second Edition, John Wiley & Sons, 1992).

The BCSP peptide of the invention is a peptide comprising an amino acid motif selected from the group consisting of "PG", "GP", "PI" and "IG" and having up to 10 amino acids upstream and/or downstream of the amino acid motif. The peptide stimulates the development, maintenance and repair of bone, cartilage and associated connective tissue. The "P" in the motif may be selected from proline and hydroxyproline.

In another embodiment, the BCSP peptide of the invention contains one or more "GP" and/or "PG" motifs and comprises up to a total of about 20 amino acids, where the peptide induces the activity of bone and cartilage cells such that bone and cartilage tissue is developed, maintained and/or repaired. The "P" of the motif can be selected from proline and hydroxyproline.

The peptides of the invention in general may have associated therewith either upstream and/or downstream of the selected motifs, a combination of the following amino acids: leucine, glycine, asparagine, isoleucine, proline, hydroxyproline, arginine, threonine, aspartate and adenine. As such, suitable amino acid sequences for use with the selected motifs may include but are not limited to,: proline, arginine, leucine, isoleucine, leucine-proline, proline-isoleucine, glycine-proline, proline-arginine, glycine-leucine, glycine-leucine-proline, glycine-leucine-proline-glycine, asparagine-glycine-leucine, asparagine-glycine-leucine-proline, proline-arginine-glycine-arginine-threonine-glycine-aspartate-alanine, proline-arginine-glycine-arginine-threonine-glycine-aspartate, proline-arginine-glycine-arginine-threonine-glycine, proline-arginine-glycine-arginine-threonine, proline-glycine-proline, asparagine-glycine-leucine-proline-glycine, asparagine-glycine-leucine-proline-glycine-proline, asparagine-glycine-leucine-proline-glycine-proline-isoleucine, proline-glycine-proline-isoleucine-glycine, proline-glycine-proline-isoleucine-glycine-proline, proline-glycine-proline-isoleucine-glycine-proline-proline and combinations thereof.

The peptide of the invention may be represented by a formula elected from the group consisting of:

$$X—(P_1)_m Gly(P_2)_n, \qquad (I)$$

$$(P_1)_m Gly(P_2)_n\text{-}Z, \text{ and} \qquad (II)$$

$$X—(P_1)_m Gly(P_2)_n\text{-}Z; \qquad (III)$$

where $P_1$ and $P_2$ are selected from the group consisting of proline and hydroxyproline, m=0 or 1, n=0 or 1, where m and n are independently selected;

X is selected from the group consisting of leucine, glycine-leucine, proline-isoleucine, glycine-proline-isoleucine, asparagine-glycine-leucine and proline-glycine-proline-isoleucine-glycine-proline; and Z is selected from the group consisting of isoleucine, arginine, isoleucine-glycine, isoleucine-glycine-proline, isoleucine-glycine-hydroxyproline, isoleucine-glycine-proline-proline, isoleucine-glycine-proline-proline-glycine, isoleucine-glycine-proline-proline-glycine-proline, isoleucine-glycine-proline-proline-glycine-proline-arginine, isoleucine-glycine-proline-proline-glycine-proline-arginine-glycine-arginine-threonine-glycine-aspartate-alanine and arginine-glycine-arginine-threonine-glycine-aspartate-alanine. In specific embodiments of the invention, the peptide is selected from the group consisting of NGLPGPIGP* (SEQ. ID. NO. 1); NGLPGPIG (SEQ. ID. NO. 2); NGLP*GPIG (SEQ. ID. NO. 3); NGLP*GPIGP* (SEQ. ID. NO. 4); NGLPGP (SEQ ID. NO. 5); LPGP (SEQ. ID. NO. 6); PGPIG (SEQ ID. NO. 7); NGLPGPIGP (SEQ. ID. NO. 8); PGPIGP (SEQ ID. NO. 9); PGPIG-PPGPR (SEQ. ID. NO. 10); GPIG (SEQ. ID. NO. 11); PGPIGPPGPRGRTGDA (SEQ. ID. NO. 12); GPRGRTGDA (SEQ. ID. NO. 13); PGPIGPP (SEQ. ID. NO. 14); PGPIGP* (SEQ. ID. NO. 15); PGPI (SEQ. ID. NO. 16); GLPGPIG (SEQ. ID. NO. 17); GPIGP* (SEQ. ID. NO. 18); GPIGP (SEQ. ID. NO. 19) and PIGP (SEQ. ID. NO. 20).

The present invention also relates to functionally equivalent variants of the peptides as described above and herein. "Functionally equivalent variants" or "functional analogues" includes peptides with partial sequence homology, peptides having one or more specific conservative and/or non-conservative amino acid changes, peptide conjugates, chimeric proteins, fusion proteins and peptide encoding nucleic acids. The functionally equivalent variants maintain the biological activity of the native peptide. The biological activity (i.e. stimulation of bone or cartilage cells) may be assessed by the analysis of one or more criteria selected from the group consisting of bone mineral density, bone mineral content, alkaline phosphatase activity, proliferation of osteoblasts, bone nodule formation, bone nodule mineralization, chondrocyte proliferation, intracellular calcium channeling assay, collagen assay and proteoglycan assay. These methods are well known and thus well within the scope of those of skill in the art (see for example U.S. Pat. Nos. 6,333,312, 5,972,623, 5,965,136, 6,030,792 and 6,060,255).

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to induce changes in connective tissue formation. A plurality of distinct peptides/proteins with different substitutions may easily be made and used in accordance with the invention. It is also understood that certain residues are particularly important to the biological or structural properties of a protein or peptide such as residues in the receptor recognition region, such residues of which may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of one polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide. Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the peptide as described herein and of any one of SEQ ID NOS. 1 to 20.

The peptide of the invention may be provided as a chimeric protein such that it contains a sequence from another protein. In one aspect, it may be desirable to provide a non native calcium binding domain of another protein to the present peptide. A chimeric peptide of the present invention may comprises a calcium binding sequence of a protein selected from the group consisting of osteopontin, dentine matrix phosphoprotein, phosvitin, phosphohoryn, beta-casein, stratherin, matrix gla protein, riboflavin binding protein and alpha S1 casein. In one embodiment, the calcium binding sequence may selected from the group consisting of S*S*, S*S*GS*EE, S*S*S*EE, S*S*S*S*S*S*, DS*S*DS*S*, S*LS*S*S*S*, DS*S*EE, DS*S*ES*, S*MS*S*S*EE and S*IS*S*S*EE and combinations thereof, where S* denotes a phosphorylated serine amino acid residue. Thus functional analogues and mimetics of such chimeric peptides are also within the scope of the present invention.

It is also within the scope of the present invention to have one or more linker molecules attached to the peptides of the invention. In aspects, the linker molecules may be attached at either or both sides (i.e. the end portions) of a selected peptide. Such linker molecules may be selected from the group consisting of carbodiimide, aldehyde, maleimide, sulfhydryl, amino, carboxy, hydroxy and NHS esters, a modified cysteine, a phosphorylated amino acid, an amino acid, diacetic acid, sulfonyl chloride, isocyanate, isothiocyanate, epoxy, bisphosphonate, pyrophosphate, phosphate, disulfide, phenyl azide, alkyl halide and hydrazide acyl chloride.

The present invention also encompasses peptides which are derived from the peptides of SEQ. ID. NO. 1, SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19 and SEQ. ID. NO. 20 but contain non-conservative amino acid changes at one or more positions, solely to the extent that such peptides are capable of providing a response in vitro, in vivo and/or ex vivo.

The peptides of the invention may be obtained by chemical synthesis using automated instruments or alternatively by expression from nucleic acid sequences which are capable of directing synthesis of the peptide using recombinant DNA techniques well known to one skilled in the art. The peptides of the invention may be prepared by chemical synthesis using techniques well known in the chemistry of proteins such as solid phase synthesis (Merrifield, J. Am. Chem. Assoc. 85:2149-2154 (1964)) or synthesis in homogenous solution (Houbenweyl, Methods of Organic Chemistry (1987), (Ed. E. Wansch) Vol. 15, pts. I and II, Thieme, Stuttgart). Techniques for production of proteins by recombinant expression are well known to those in the art and are described, for example, in Sambrook et al. (1989) or latest edition thereof.

The present invention also contemplates non-peptide analogues of the peptides of the invention, e.g. peptide mimetics that provide a stabilized structure or lessened biodegradation. Peptide mimetic analogues can be prepared based on a selected BCSP peptide having a sequence selected from SEQ. ID. NO. 1, SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19 or SEQ. ID. NO. 20, by replacement of one or more residues by non-peptide moieties. Preferably, the non-peptide moieties permit the peptide to retain its natural conformation, or stabilize a preferred, e.g. bioactive confirmation. Such peptides can be tested in molecular or cell-based binding assays to assess the effect of the substitution(s) on conformation and/or activity. The preparation of non-peptide mimetic analogues from the peptides of the invention can be done, for example, as taught in Nachman et al., *Regul. Pept.*57: 359-370 (1995).

The present invention also encompasses nucleic acid molecules comprising a nucleotide sequence which encodes one or more of amino acid sequences selected from SEQ. ID. NO. 1, SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, SEQ. ID. NO. 9 SEQ. ID. NO. 10, SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19 or SEQ. ID. NO. 20 as well as variants thereof.

Also encompassed by the present invention are nucleic acid sequences which are complementary as well as anti-complementary to a sequence encoding and equivalent sequence variants thereof. One skilled in the art would readily be able to determine such complementary or anti-complementary nucleic acid sequences. Also as part of the invention are nucleic acid sequences which hybridize to one of the aforementioned nucleic acid molecules under stringent conditions. "Stringent conditions" as used herein refers to parameters with which the art is familiar and such parameters are discussed, for example, in the latest editions of Molecular Cloning: A Laboratory Manual, J. Sambrook, et al., eds., Cold Spring Harbor Laboratory Press, Cold Spring Harbor, N.Y., or Current Protocols in Molecular Biology, F. M. Ausubel, et al., eds., John Wiley & Sons Inc., New York. One skilled in the art would be able to identify homologues of nucleic acids encoding the BCSP peptides of the invention. Cells and libraries are screened for expression of such molecules which then are routinely isolated, followed by isolation of the pertinent nucleic acid molecule and sequencing.

It is noted that the nucleic acid molecules described herein may also encompass degenerate nucleic acids. Due to degeneracy in the genetic code, variations in the DNA sequence will result in translation of identical peptides. It is thus understood that numerous choices of nucleotides may be made that will lead to a sequence capable of directing production of the peptides or functional analogues thereof of the present invention. As a result, degenerative nucleotide substitutions are included in the scope of the invention.

As would be understood by one of skill in the art, nucleic acid molecules of the present invention may encompass single and double stranded forms, plasmid(s), viral nucleic acid(s), plasmid(s) bacterial DNA, naked/free DNA and RNA. A viral nucleic acid comprising a nucleic acid sequence encoding for at least one peptide of the invention may be referred to as a viral vector.

The invention also encompasses expression vectors comprising the nucleic acid sequences of the invention encoding one or more of the peptides of SEQ ID NO. 1 to 20 and functional analogues thereof within expression vectors. Any expression vector that is capable of carrying and expressing the nucleic acid sequences encoding for the peptides of the invention and functional analogues thereof in prokaryotic or eukaryotic host cells may be used, including recombinant viruses such as poxvirus, adenovirus, alphavirus and lentivirus.

The invention also encompasses host cells transformed, transfected or infected with such vectors to express the peptides or functional analogues of the invention. As such, host cells encompass any potential cell into which a nucleic acid of the present invention may be introduced and/or transfected.

Compositions

With the demonstration that one or more of the peptides of the present invention can directly affect connective tissue formation in vitro, in vivo, or ex vivo and in particular possess osteogenesis-promoting activity or chondrogenesis-promoting activity that is influential in tissue repair and tissue engineering, pharmaceutical compositions can now be developed and used in order to treat skeletal trauma, skeletal development abnormalities (both non-metabolic bone diseases and metabolic bone diseases), arthritis and degenerative joint diseases.

Representative uses of the peptides of the present invention for bone trauma or bone development abnormalities include for example repair of bone defects and deficiencies, such as those occurring in closed, open and non-union fractures, bone/spinal deformation, osteosarcoma, myeloma, bone dysplasia and scoliosis; prophylactic use in closed and open fracture reduction; promotion of bone healing in plastic surgery; stimulation of bone ingrowth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis or disuse osteoporosis and arthritis, osteomalcia, fibrous osteitis, renal bone dystrophy and Paget's disease of bone, or any condition that benefits from stimulation of bone formation.

The peptides of the present invention may also be used in therapeutic applications in the stimulation of new cartilage formation. Representative uses of the peptides of the present invention for cartilage trauma or cartilage abnormalities include cartilage sports injuries such as torn cartilage; cartilage defects such as cartilage lesions and osteochondral defects; and degenerative cartilage diseases such as osteoarthritis One skilled in the art would be able to use the peptide compositions as described herein to treat and alleviate the aforementioned trauma and diseases and have a reasonable expectation of success with respect to a positive physiological effect on a variety of cell types including but not limited to bone cells (i.e. osteoblasts, pre-osteoblasts and cells sharing lineage therewith) cartilage cells (i.e. chondrocytes, pre-chondrocytes and cells sharing lineage therewith), and skeletal progenitor cells derived from bone, bone marrow or blood. Further, any number of agents such as bone morphogenetic factors, anti-resorptive agents, osteogenic factors, cartilage morphogenetic factors, growth hormones and differentiating factors may be used together with the peptide compositions of the invention in order to aid in the promotion of connective tissue development, maintenance and repair.

The compositions of the present invention can be useful in repair of congenital, trauma-induced or surgical resection of connective tissue (for instance, for cancer treatment), and in cosmetic surgery. Such tissue deficit or defect can be treated in vertebrate subjects by administering the peptides of the invention which exhibit certain structural and functional characteristics.

The peptides of the invention may be used for skeletal reconstruction involving ex vivo tissue engineering of cartilage and/or bone tissue for implantation in a vertebrate. Cells and/or developing tissues can be treated in vitro with a selected peptide(s) or functional analogue thereof during the tissue engineering process to promote any or all the steps of cell proliferation, cell differentiation, and/or tissue construct formation. The cell source for the tissue engineering process may be autologous, allogenic, or xenogenic. The ex vivo process may be concluded after cell expansion, cell differentiation or tissue construct formation, and the cells and/or tissues so produced introduced into the patient. The use of tissue engineering techniques enables the formation of de novo tissue that reduces or eliminates the requirement to obtain autograft, allograft or xenograft tissue. Such practice is highly desirable as each of these tissue sources has attendant complications. The autograft procedure commonly results in donor site morbidity, while the use of allograft carries the risk of infection and xenograft has the potential to induce immunological complications. The compositions of the invention may be administered systemically or locally. For systemic use, the compounds herein are may be formulated for administration selected from intravenous, subcutaneous, intramuscular, intraperitoneal, oral, enteral, parenteral, intranasal, pulmonary, topical or transdermal administration according to conventional methods. For example, the composition may be prepared for local administration by intra-articular injection or use with an implant.

For oral administration the compositions may be in the form of a liquid preparation, or may be filled in soft capsules or like to yield an oral preparation when it is obtained in a liquid form. When the composition of the present invention is in a solid dispersion, it can be packed in capsules or shaped into pellets, fine granules, granules or tablets to yield an oral preparation. As a solid dispersion, the composition may be shaped into solid forms such as spheres, rods, needles, pellets and films in the presence of additional additives as necessary as is understood by one skilled in the art.

Intravenous administration can be by a series of injections or by continuous infusion over an extended period. Administration by injection or other routes of discretely spaced administration can be performed at intervals ranging from weekly to once to three times daily. Alternatively, the peptides disclosed herein may be administered in a cyclical manner (administration of disclosed peptide; followed by no administration; followed by administration of disclosed peptide, and the like). Treatment may continue until the desired outcome is achieved.

The peptide compositions are administered in a therapeutically effective dose in accordance with the invention. A therapeutic concentration will be that concentration which effects the desired level of tissue formation or local tissue repair; or the reduction of a particular condition or the rate of expansion of such condition. A useful therapeutic or prophylactic concentration will vary from condition to condition and in certain instances may vary with the severity of the condition being treated and the patient's susceptibility to treatment. Accordingly, no single concentration may be uniformly useful, but will require modification depending on the particularities of the chronic or acute condition being treated. Such concentrations can be arrived at through routine experimentation as is known to those of skill in the art.

In general, pharmaceutical formulations will include a peptide(s) of the present invention in combination with a pharmaceutically acceptable vehicle, such as saline, buffered saline, 5% dextrose in water, ethanol, borate-buffered saline containing trace metals or the like and mixtures thereof. Formulations may further include one or more excipients, preservatives, solubilizers, buffering agents, albumin to prevent protein loss on vial surfaces, lubricants, fillers, stabilizers, etc. Methods of \formulation are well known in the art and are disclosed, for example, in Remington's Pharmaceutical Sciences, Gennaro, ed., Mack Publishing Co., Easton Pa., 1990, which is incorporated herein by reference.

The compositions of the present invention can be used concomitantly with other agents for treating bone diseases. Examples of drugs concomitantly used may include for example, calcium preparations (e.g. calcium phosphate, calcium sulfate, calcium carbonate), calcitonin preparations, sex hormones (e.g. estrogen, estradiol), prostaglandin A1, bisphosphonic acids, ipriflavones, fluorine compounds (e.g. sodium fluoride), vitamin K, fibrin, proteoglycans, bone morphogenetic proteins (BMPs), fibroblast growth factor (FGF), platelet-derived growth factor (PDGF), transforming growth factor (TGF-$\beta$), insulin-like growth factors 1 and 2 (IGF-1, 2), endothelin, parathyroid hormone (PTH), epidermal growth factor (EGF), leukemia inhibitory factor (LIP), osteogenin, and bone resorption repressors such as estrogens, calcitonin and biphosphonates. It is also contemplated that mixtures of such agents may also be used and formulated within the compositions of the present invention or used in conjuction with the compositions of the present invention.

Pharmaceutical compositions for use within the present invention can be in the form of sterile, non-pyrogenic liquid solutions or suspensions, coated capsules, creams, lotions, lyophilized powders or other forms known in the art. The peptides of the invention may be formulated into a hydrogel for local adminstration or for application to a desired carrier. Local administration may be by injection at the site of injury or defect, or by insertion or attachment of a solid carrier at the site. For local administration, the delivery vehicle may provide a matrix or scaffold for the ingrowth of bone or cartilage, and may be a vehicle that can be absorbed by the subject without adverse effects.

In one preferred embodiment, the peptides of the invention may be used in conjunction with a synthetic biomaterial compound (Skelite™, described in Applicant's U.S. Pat. No. 6,323,146 and herein incorporated by reference). This isolated bioresorbable biomaterial compound comprises calcium, oxygen and phosphorous, wherein a portion of at least one of said elements is substituted with an element having an ionic radius of approximately 0.1 to 0.6 Angstroms. In this embodiment, the synthetic biomaterial compound may be shaped into a desired three-dimensional implant and the peptide composition provided as a coating thereon or as a matrix dispersed therein. Alternatively, the peptide composition may be intimately mixed with a granular or powdered form of Skelite™ for localized administration.

A variety of polymers can be used to form an implant for the purposes of delivering the peptide composition of the invention to a desired in vivo site. Suitable polymers include but are not limited to polyesters, polyvinyl acetate, polyacrylates, polyorthoesters, polyhydroxyethylmethacrylate(polyhema) and polyanhydrides. Certain of the polymers can be selected based on the properties of being both biodegradable and biocompatible. Aliphatic polyesters derived from lactide, glycolide, and -caprolactone monomers are especially favourable since they possess a fairly broad range of degradation profiles. The peptide compositions of the invention may be used in conjunction with collagen, fibrins, starches, alginate, and hyaluronic acid.

In addition to the polymers and carriers noted above, the biodegradable films and matrices incorporating the peptide compositions may include other active or inert components and mixtures thereof as discussed supra. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and the like. Agents that promote bone growth, such as bone morphogenetic proteins (U.S. Pat. No. 4,761,471), osteogenin (Sampath et al. Proc. Natl. Acad Sci USA (1987) 84:7109-13) and NaF (Tencer et al. J. Biomed. Mat. Res. (1989) 23: 571-89) are also preferred. Biodegradable films or matrices include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials (for example polymer implants, titanium implants), to provide desired biological, mechanical, cosmetic, or matrix interface properties.

In one aspect, the delivery of the peptides described herein to desired sites may be enhanced by the use of controlled-release compositions, such as those described in WIPO publication WO 93/20859 (which is incorporated herein by reference in its entirety). Films of this type are particularly useful as coatings for both resorbable and non-resorbable prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

Alternative methods for delivery of compounds of the present invention include use of ALZET osmotic minipumps (Alza Corp., Palo Alto, Calif.); sustained release matrix materials such as those disclosed in Wang et al. (PCT Publication WO 90/11366); electrically charged dextran beads, as disclosed in Bao et al. (PCT Publication WO 92/03125); collagen-based delivery systems, for example, as disclosed in Ksander et al. Ann. Surg. (1990) 211 (3):288-94; methylcellulose gel systems, as disclosed in Beck et al. J. Bone Min. Res. (1991) 6(11): 1257-65; alginate-based systems, as disclosed in Edelman et al. Biomaterials (1991) 12:619-26 and the like. Other methods well known in the art for sustained local delivery in bone include porous coated metal prostheses that can be impregnated and solid plastic rods containing therapeutic compositions of the present invention.

In one embodiment, the peptide composition may comprise at least one peptide selected from SEQ ID NO. 1-20 provided as a solution or emulsion contained within phospholipid vesicles called liposomes. The liposomes may be unilamellar or multilamellar and are formed of constituents selected from phosphatidylcholine, dipalmitoylphosphatidylcholine, cholesterol, phosphatidylethanolamine, phosphatidylserine, demyristoylphosphatidylcholine and combinations thereof. The multilamellar liposomes comprise multilamellar vesicles of similar composition to unilamellar vesicles, but are prepared so as to result in a plurality of compartments in which the selected peptide in solution or emulsion is entrapped. Additionally, other adjuvants and modifiers may be included in the liposomal formulation such as polyethylene glycol, or other materials.

It is understood by those skilled in the art that any number of liposome bilayer compositions can be used in the composition of the present invention. Liposomes may be prepared by a variety of known methods such as those disclosed in U.S. Pat. No. 4,235,871 and in RRC, Liposomes: A Practical Approach. IRL Press, Oxford, 1990, pages 33-101.

The liposomes containing the peptides of the invention may have modifications such as having non-polymer molecules bound to the exterior of the liposome such as haptens, enzymes, antibodies or antibody fragments, cytokines and hormones and other small proteins, polypeptides or non-protein molecules which confer a desired enzymatic or surface recognition feature to the liposome. Surface molecules which preferentially target the liposome to specific organs or cell types include for example antibodies which target the liposomes to cells bearing specific antigens. Techniques for coupling such molecules are well known to those skilled in the art (see for example U.S. Pat. No. 4,762,915). Alternatively, or in conjunction, one skilled in the art would understand that any number of lipids bearing a positive or negative net charge may be used to alter the surface charge or surface charge density of the liposome membrane.

The liposomes can also incorporate thermal sensitive or pH sensitive lipids as a component of the lipid bilayer to provide controlled degradation of the lipid vesicle membrane.

For systemic application by intravenous delivery, it may be beneficial to encapsulate the peptides of the invention within sterically-stabilized liposomes which exhibit prolonged circulation time in blood. The sterically stabilized liposomes are produced containing polyethylene glycol as an essential component of their surface and the method of making such liposomes is known to those skilled in the art.

The size of the liposomes can be selected based on the intended target and route of administration. Liposomes of between about 10 nm to 300 nm may be suitable. Furthermore, the composition of the present invention may include liposomes of different sizes.

While the composition of the present invention may be encapsulated for administration by liposomes, it is understood by those skilled in the art that other types of encapsulants may also be used to encapsulate BCSPs of the invention. Microspheres including but not limited to those composed of ion-exchange resins, crystalline ceramics, biocompatible glass, latex and dispersed particles are suitable for use in the present invention. Similarly, nanospheres and other lipid, polymer or protein materials can also be used.

The peptides of the invention, as provided alone or in a composition, may also be used in vitro to stimulate the activity of bone cells and/or cartilage cells, such cells then being administered to a mammal in order to treat a bone or cartilage disorder/defect.

The invention also provides methods for the screening and identifying further functional analogues of the peptides where such identified peptides have essentially the activity of the peptides as described herein. Such screening involves contacting a biological sample that is capable of undergoing bone and/or cartilage formation with a test peptide or compound and then separately contacting a second biological sample that is also capable of undergoing bone and/or cartilage formation with an amount of one or more of a peptide of SEQ ID. NO. 1 to SEQ. ID. NO. 20. The level of bone and/or cartilage formation is then assessed by the analysis of one or more criteria selected from the group consisting of bone mineral density, bone mineral content, alkaline phosphatase activity, proliferation of osteoblasts, bone nodule formation, bone nodule mineralization, chondrocyte proliferation, intracellular calcium channeling assay, collagen assay and proteoglycan assay. The levels of bone and/or cartilage formation are then compared in each biological sample in order to identify whether the test peptide or compound has essentially the activity of the peptides of the invention. Using a similar approach, modulators of the bone and/or cartilage formation can also be assessed.

In summary, the peptide(s) of the invention are influential in the development, maintenance and repair of connective tissue which includes not only bone, but also cartilage and related connective tissues.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide biochemistry, molecular biology, histology and immunology referred to but not explicitly described in this disclosure and examples are reported in the scientific literature and are well known to those skilled in the art.

Example 1

BCSP1 and Skelite™ Carrier for Implant Applications

The performance of BCSP1 in a bone repair application was evaluated in vivo using critical size defects created in the ulnae of skeletally mature New Zealand White (NZW) rabbits, as described by Bolander et al. (J. Bone and Joint Surg., 68-A (8), October 1986). Autograft, harvested from the iliac crest served as the contralateral control. Rabbits from the study group and the control group were terminated at 12 weeks.

BCSP1 was bound to Skelite™ implant by dissolving 9.0 mg of the peptide in 0.15 ml of water and lyophilizing it onto the surface of the implant thus creating a Skelite™/BCSP1 implant. Animals were anesthetized using intramuscular injections of Fentanyl (0.3 mg/kg) and Midazolam (2.0 mg/kg). Full section ulnar critical size defects, measuring 2 cm in length, were created using a hall micros sagittal saw (Model 100, Blade No. 5023-160). Care was taken to ensure that 'scoring' or cutting of the neighboring radius did not occur as such damage could act as a stress riser and fracture of the radius could result.

Bone marrow, percutaneously harvested from the greater trochanter of the femur using an 18 gauge needle, was administered to the surfaces of each porous Skelite™/BCSP1 implant (6×4×20 mm). This was accomplished by placing the Skelite™/BCSP1 implant into a sterile petri dish containing a pool of marrow aspirate and rotating the implant every minute for 4 minutes while the ulnar defect was being created. After the Skelite™/BCSP1 implant graft had been implanted into the recipient bed of the right forelimb, and prior to closure of the wound, an additional 0.5 ml of bone marrow aspirate was applied to the surface of the Skelite™/BCSP1 implant using a syringe. Autologous bone, harvested from the iliac crest using standard orthopaedic techniques, was trimmed to the appropriate dimensions and implanted into the left forelimb defect. Following standard clinical practice, the autografts were not supplemented with bone marrow aspirate.

Animals were euthanized at 12 weeks by intravenous overdose using 2 ml of Euthanyl. The forelimbs were excised and the surrounding musculature was removed. After visual inspection, the excised bones (both radius and ulna) were fixed in either 70% Ethanol or 100% Formalin and analyzed using histological and bone densitometry techniques.

A cortex-like structure or callus was noted in proximity to the Skelite™/BCSP1 implants in all animals. The cortical shell was bridging both ends of the ulna surrounding the implant. This neo-cortical structure had a lamellar pattern under polarized light. Fatty marrow-like tissue was noted between the neo-cortex and the Skelite™/BCSP1 implant. Similarly, a marrow-like tissue was noted between the Skelite™/BCSP1 implant and the radius.

All Skelite™/BCSP1 implant treated defects exhibited excellent osteointegration and substantial bone formation throughout the porous structure of all Skelite™/BCSP1 implants with integration between the host bone and the implant at both ends of the defect. Unlike the contralateral controls, all of the defects treated with Skelite™/BCSP1 implants achieved union by 9 weeks post surgery (FIG. 1). In addition, microscopic histological observation identified extensive osteoclastic resorption of the Skelite™ material and the formation of tissue within the triangular voids of the Skelite™ 'struts'.

Figure 2:
FIG. 2 shows a radiograph illustrating the performance of Skelite™/BCSP1 implant versus autograft at 9 weeks post surgery.

For defects treated with Skelite™/BCSP1 implants, histopathological observations at 12 weeks consistently demonstrated marked to massive osteointegration, slight formation of woven bone, moderate formation of lamellar bone, the formation of a medullary-like cavity, the formation of a psuedo-cortex, and union (FIG. 2). In contrast, microscopic findings of defects treated with autograft exhibited evidence of psuedoarthrosis, bone sequestrum, marrow necrosis/fibrosis, and interosseous union.

Critical size defects treated with Skelite™/BCSP1 implants exhibited accelerated rates of healing when compared to defects treated with autologous bone. This accelerated rate of healing was evident in radiographs as early as 3 weeks post surgery and substantial callus formation was observed in all defects treated with Skelite™/BCSP1 implants. Defects treated with Skelite™/BCSP1 typically exhibited radiographic evidence of union 6 weeks post surgery. Ongoing healing of the Skelite™/BCSP1 implant treated defects involved continued callus formation, remodelling of the callus, and the development of a cortical shell encompassing the entire implant. By 9 weeks all of the defects treated with Skelite™/BCSP1 implants had structural union and callus remodelling was prevalent. Excellent integration and strong union between the Skelite™/BCSP1 implant and the host bone was evident at termination. These radiographic results were corroborated by bone mineral density scans of the excised bones.

Histological evaluation indicated osteointegration for all defects treated with Skelite™/BCSP1 implants. Unlike autologous bone which resulted in only partial healing of the defect with psuedoarthrosis, bone sequestrum, and marrow necrosis/fibrosis, the defects treated with Skelite™/BCSP1 implants exhibited solid bone union, a high level of osteointegration, and the formation of both cortical shells and marrow-like cavities. Mature, lamellar bone was observed in direct contact with the Skelite™/BCSP1 material (in the absence of a fibrous tissue membrane interface) and a high level of osteoclastic activity was noted. Scalloped resorption lacunae and 'cutting cones' were frequently observed on both the external and internal surfaces of all Skelite™/BCSP1 implants.

Figure 3:
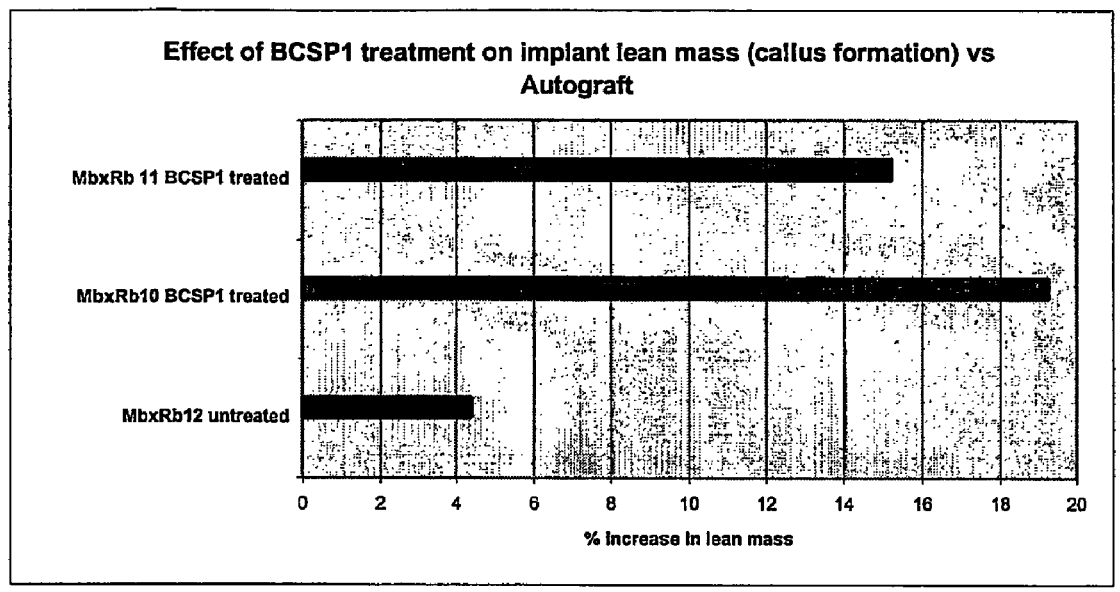
FIG. 3 shows the effects of BCSP1 treatment on implant lean mass (callus formation) versus autograft.

For defects treated with Skelite™/BCSP1 implants, callus formation was also analyzed in order to provide a further quantifiable parameter for increased tissue formation at the site of the implant. The increase in callus formation on the segmental defect rabbit model was measured using DEXA analysis of lean mass (this excludes mineral mass). Quantitative changes in lean mass indicates changes in callus or soft tissue formation in the scanned region of the Skelite™/BCSP1 implant (FIG. 3).

These results suggest that the treatment of critical bone defects in rabbits with Skelite™/BCSP1 implants resulted in significant bone repair compared to autograft controls.

Example 2

BCSP1, BSCP7, BSCP9 and BSCP10 effects on BMC and BMD

BCSP1 peptide and BCSP4 peptide were tested at four dose levels, 0.05, 0.5, 1.0 & 5.0 mg/rat or vehicle, n=6 per dose. Sixty male Wistar rats, weighing 90-110 grams, were randomized into two groups, ear tagged and left undisturbed for 1 week prior to the procedure. Food and water are administered ad libitum. Animals weighed 150-190 grams at time of injection. Group 1 received injections of BCSP4 peptide on day 8 of acclimation. Group 2 received injections of BCSP1 peptide on day 9 of acclimation. Dissections were conducted on respective days, 7 days post injection.

The peptides were dissolved in sterile water at 0.05-5 mgs per 100 microliter volume, added to 0.5 mg of dry Skelite™ powder and lyophilized onto the carrier. Samples are resuspended in 100 microliters of sterile saline for injection. Delivery of the test compound was made under a general anaesthetic of Isofluorane with oxygen. Using a 0.5 cc insulin syringe fitted with a 28G½" needle, the peptides were deposited onto the periosteal surface of the right medial tibia surface proximal to the knee under the Tibialis cranialis muscle group. Control animals are injected with saline vehicle and Skelite™ carrier.

Figure 4:
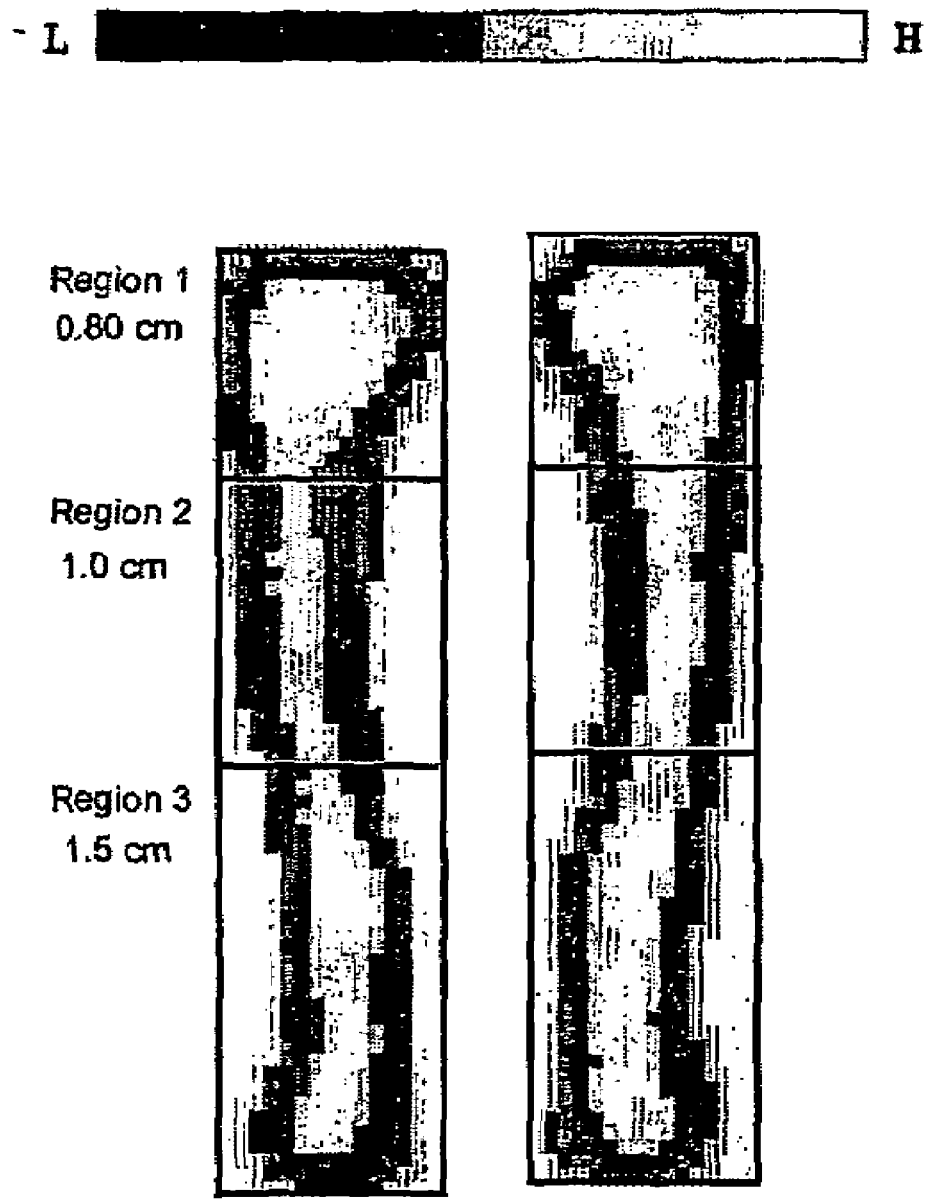
FIG. 4 shows DEXA analysis regions of tibia injected with BCSP1 peptide. Whole bone analysis includes all three regions of the tibia. BCSP1 peptide injection is administered in Region 2.
Figure 6:
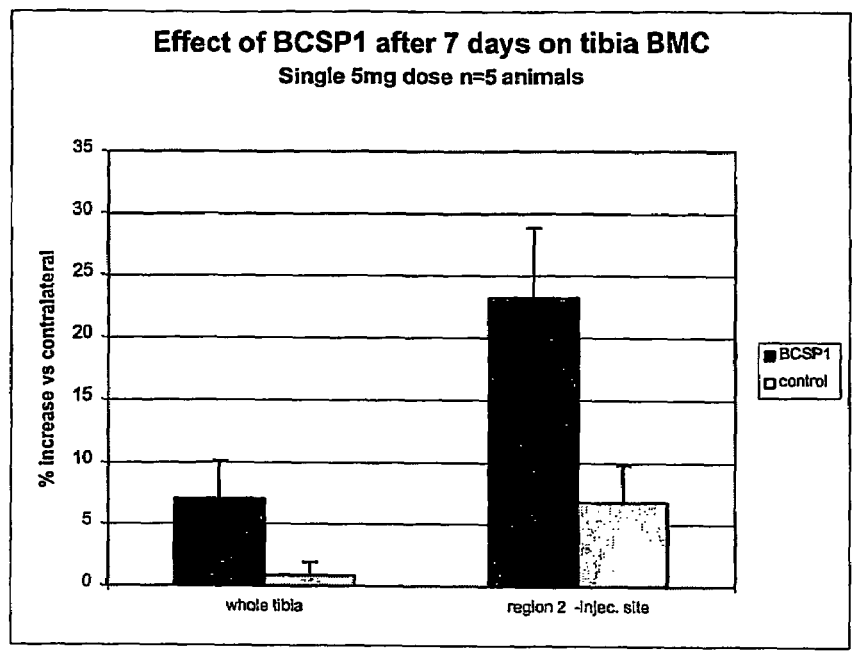
FIG. 6 shows the effect of BCSP1 on bone mineral content (BMC) of the whole tibia versus the localized effect of BCSP1 on region 2 within the tibia.
Figure 5:
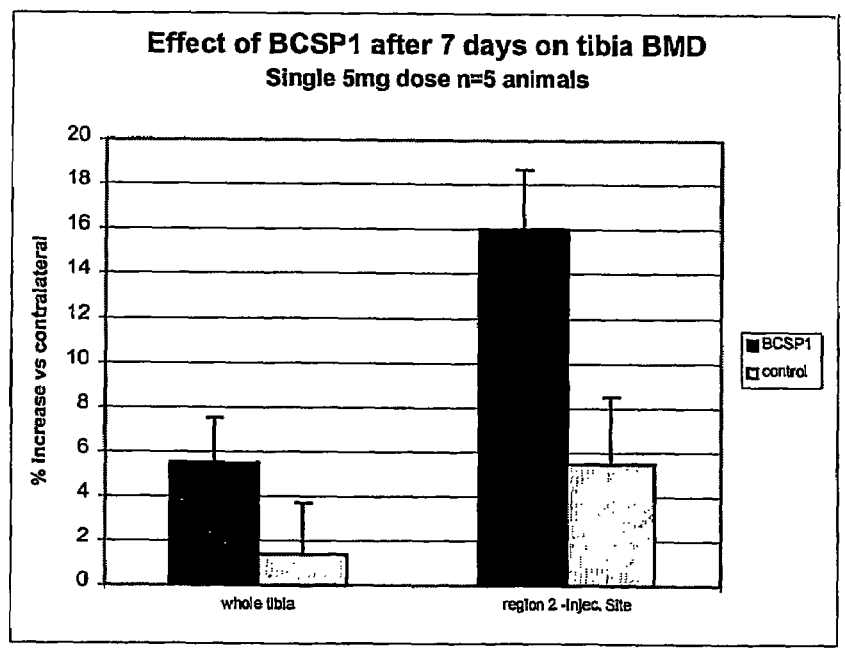
FIG. 5 shows the effect of BCSP1 on bone mineral density (BMD) of the whole tibia versus the localized effect of BCSP1 on region 2 within the tibia.
Figure 7A:
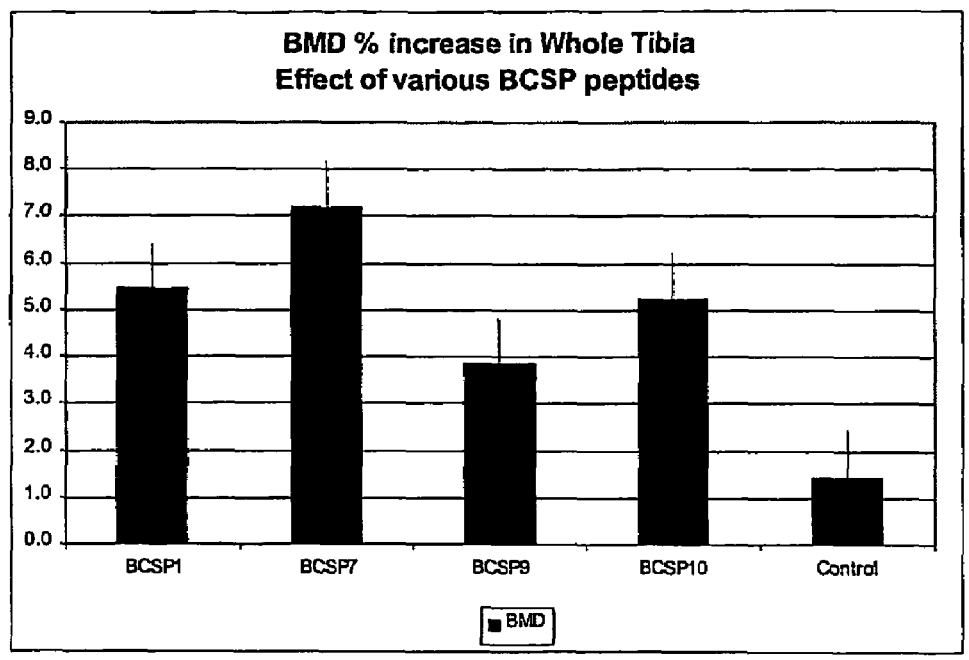
FIG. 7A shows the average increase in bone mineral density for whole tibia for BCSP1, BCSP7, BCSP9, BCSP10 and control.
Figure 7B:
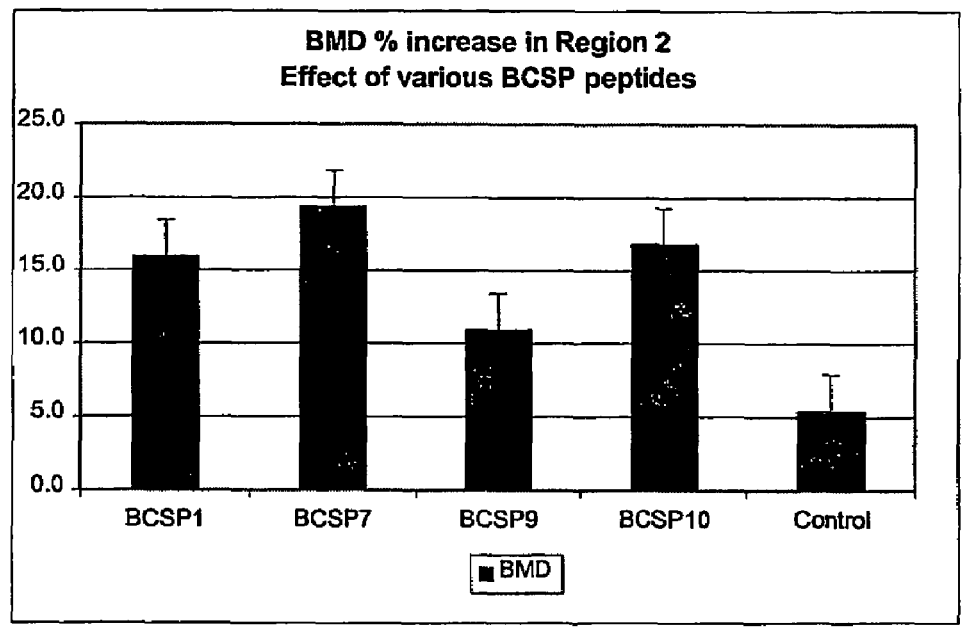
FIG. 7B shows the average increase in bone mineral density for region 2 of the tibia (see FIG. 4) for BCSP1, BCSP7, BCSP9, BCSP10 and control.
Figure 8A:
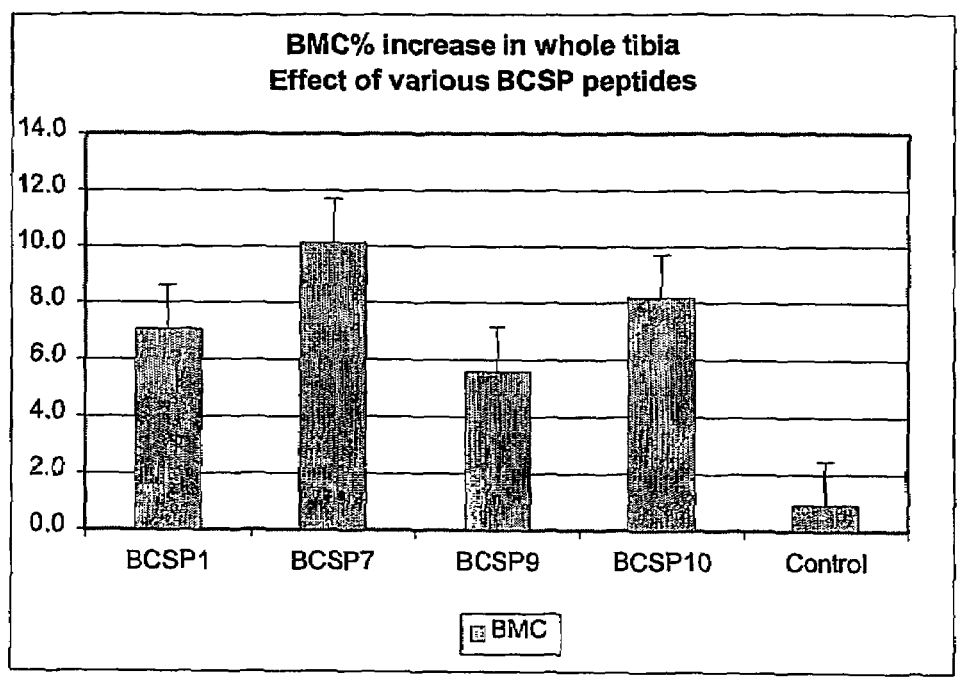
FIG. 8A shows the average increase in bone mineral content for whole tibia for BCSP1, BCSP7, BCSP9, BCSP10 and control.
Figure 8B:
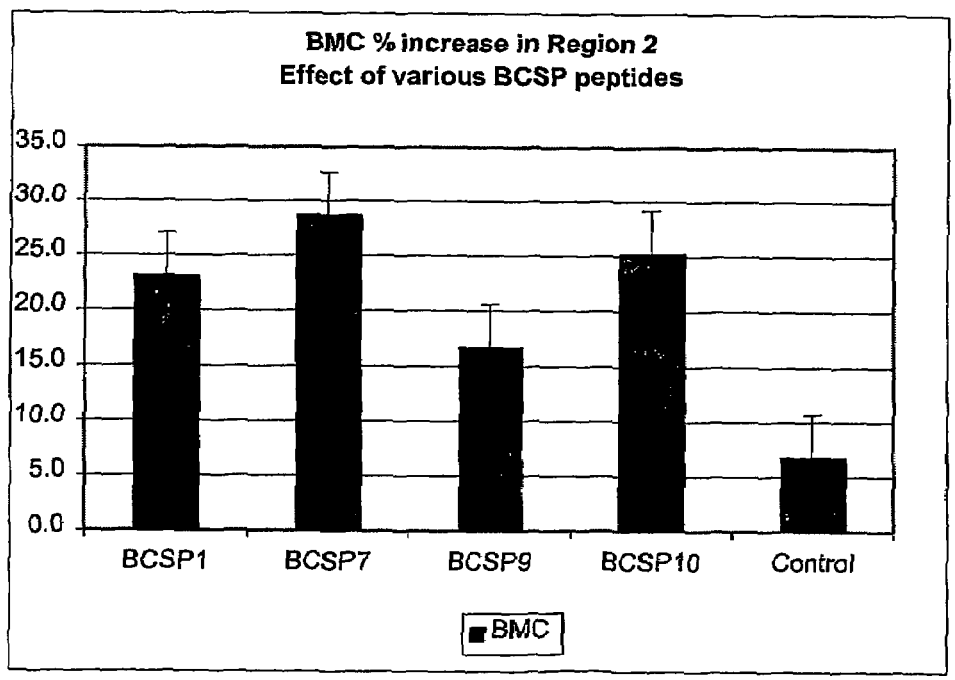
FIG. 8B shows the average increase in bone mineral content for region 2 of the tibia (see FIG. 4) for BCSP1, BCSP7, BCSP9, BCSP10 and control.

Animals were euthanized with carbon dioxide and dissected to remove the treated right tibia and contra-lateral control limb, 7 days post injection. Muscle and soft connective tissue is dissected away prior to fixation in 70% ethanol. Each tibia set was scanned as a pair for bone mineral density (BMD) and bone mineral content (BMC) on a Norland Eclipse DEXA scanner in small subject mode. DEXA analysis regions are shown in FIG. 4. Percent increases in local BMD (FIG. 5) were calculated against the untreated contra-lateral limb. Increases in BMC (FIG. 6) were also determined as a measure of bone forming activity independently of BMD due to the increase in bone size that is seen with BCSP1. This increase in physical size reduces the overall percentage increase in BMD (BMD=BMC/cm$^2$). Each tibia was analyzed in 3 contiguous regions, proximal, medial and distal as well as whole tibia measurements. Comparisons and statistical assessment of dose versus vehicle were conducted for each peptide for bone forming activity using a standard student t-test.

Significant changes in BMD and BMC were also demonstrated for BCSP7, BCSP9 and BCSP10 in treated whole tibia in all regions (FIGS. 7A, 7B, 8A and 8B).

Example 3

BCSP1 Effects on Chondrocytes

BCSP1 was tested in vitro to determine effect on bovine and human primary chondrocyte cultures using a [3H] thymidine incorporation assay. Cells were seeded at 250,000/well for bovine chondrocytes; 500,000/well for human chondrocytes (96 well plate) and allowed to attach for 48 h (medium containing 10% fetal bovine serum (FBS). Preconfluent cells were then treated in quaduplicate with BCSP1 (0, 10, 20 and 40 ng/ml for 48 hrs and with [3H]thymidine (1 Ci/ml) for the last 24 hrs (medium containing 2% FBS). The culture medium used was Dulbecco's Modified Eagle Medium (DMEM) (Gibco, Cat.#23800) containing 200 units/ml Penicillin, 200 ug/ml Streptomycin and 10% FBS for growth and 2% FBS for dosing.

Figure 9:
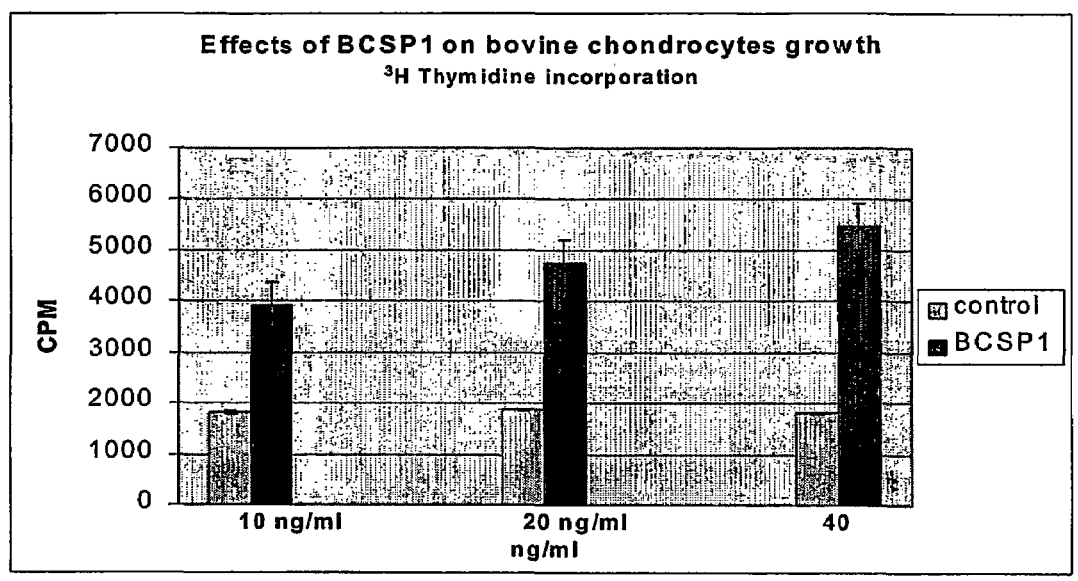
FIG. 9 shows the effects of BCSP1 on bovine chondrocyte growth.
Figure 10:
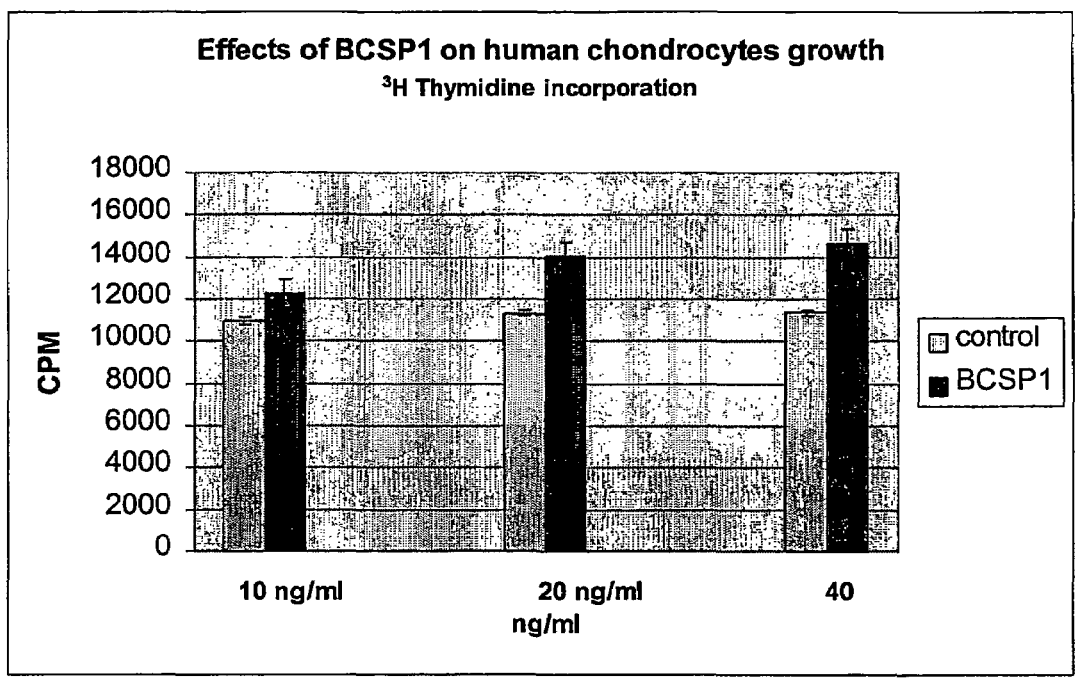
FIG. 10 shows the effects of BCSP1 on human chondrocyte growth.

Results demonstrate the dose dependent increase in proliferation of human or bovine chondrocyte cells when treated with BCSP1 in vitro. Effect is up to 3 fold with doses in the nanogram range (FIGS. 9 and 10).

Example 4

In vitro Assays using BCSP1 Peptide

BCSP1 was tested in three assays to understand the mechanism of bone stimulation by the peptide. Dose ranges in the microgram range were used to generate dose response curves. All assays used primary rat osteoblast cultures from bone marrow or calvaria.

Osteoblast proliferation was accessed using a DNA based assay which measures bromodeoxyuridine (BrdU) incorporation. Differentiation of osteoblasts was detemined using the mid to late stage bone marker Alkaline Phosphatase. Late stage differentiation and mineralization was determined using a Bone Nodule formation assay (calvaria only).

Figure 11:
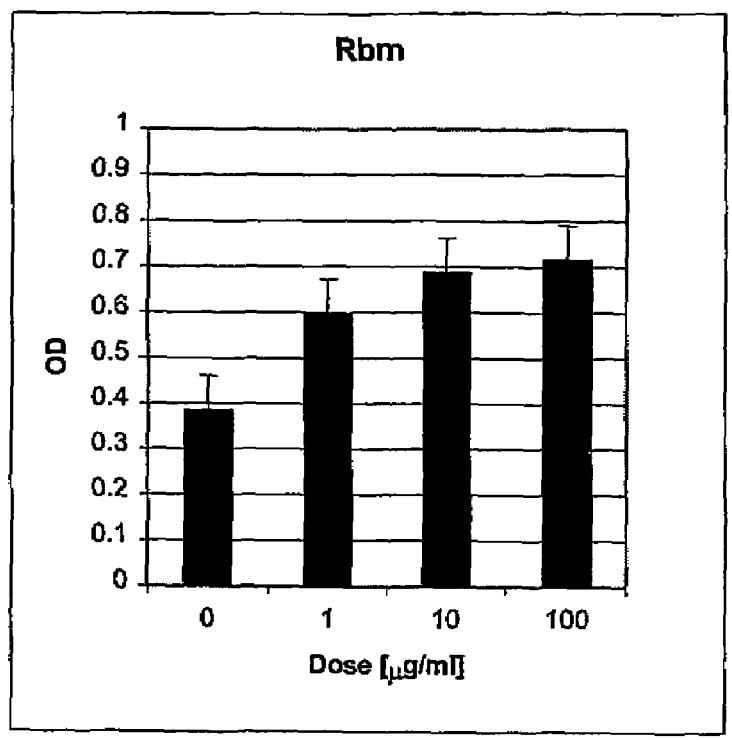
FIG. 11 shows the effects of BCSP1 on DNA synthesis in rat bone marrow derived osteoblast cultures.

Osteoblast cultures derived from rat bone marrow exhibited increased proliferation in response to the presence of BCSP1. Cells were cultured for four days prior to a 24 hr exposure to the peptide (FIG. 11). A dose response increase in osteoblast proliferation was observed to 100 μg/ml. This demonstrated that the addition of BCSP1 resulted in up to a 75% increase in DNA synthesis.

Figure 12:
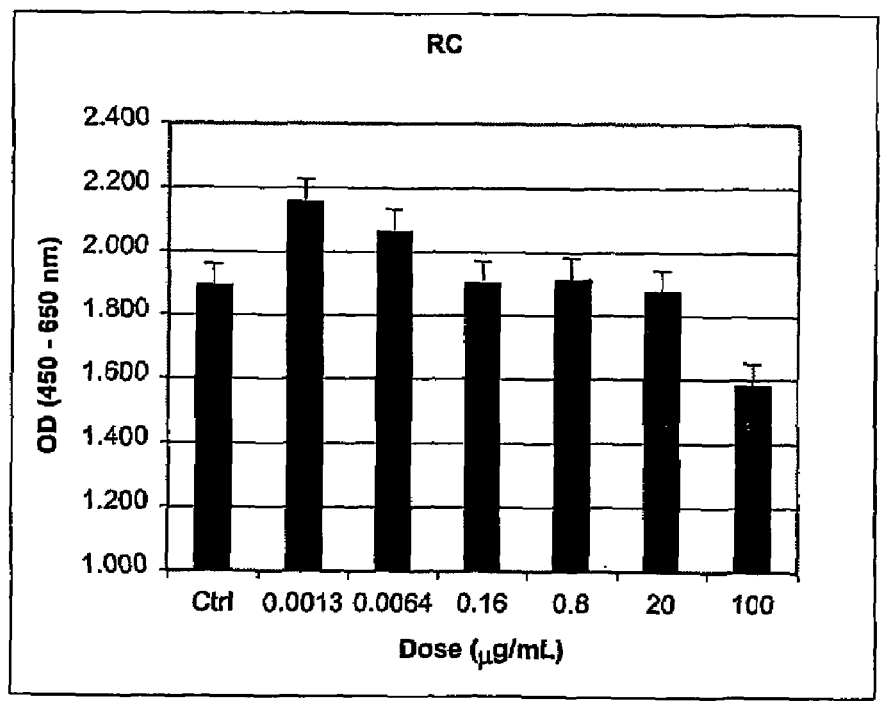
FIG. 12 shows the effects of BCSP1 on proliferation of calvaria derived osteoblast cultures.

Osteoblast cultures derived from rat calvaria also exhibited increased proliferation in response to the presence of BCSP1. Cells were cultured for four days prior to a 24 hr exposure to the peptide at a dose range from 100 μg/ml to 1.3 ng/ml of peptide (FIG. 12). An inverted dose response was observed at higher doses. A statistically significant increase was observed at a dose range of 1.3-6.4 ng/ml of peptide.

Figure 13:
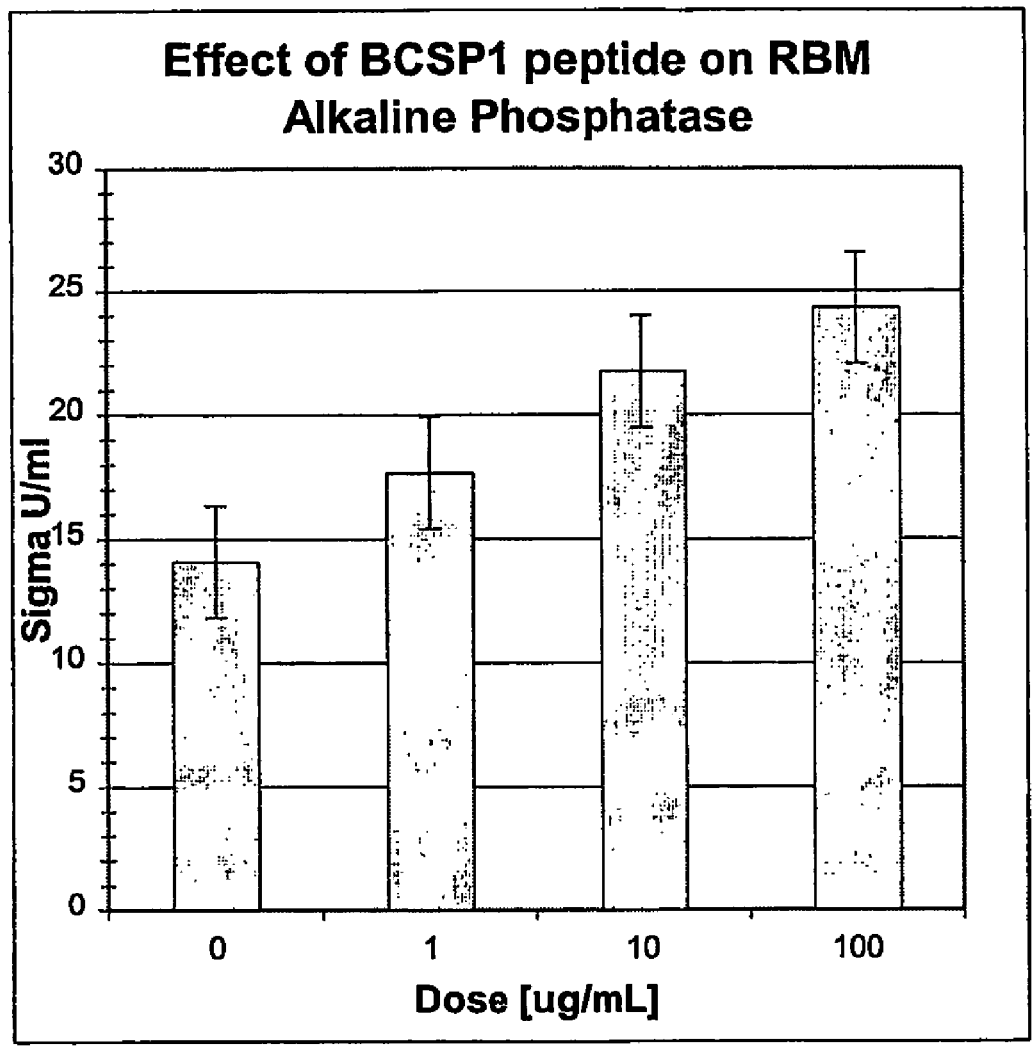
FIG. 13 shows the effects of BCSP1 on alkaline phosphatase activity in bone marrow derived osteoblasts.
Figure 14:
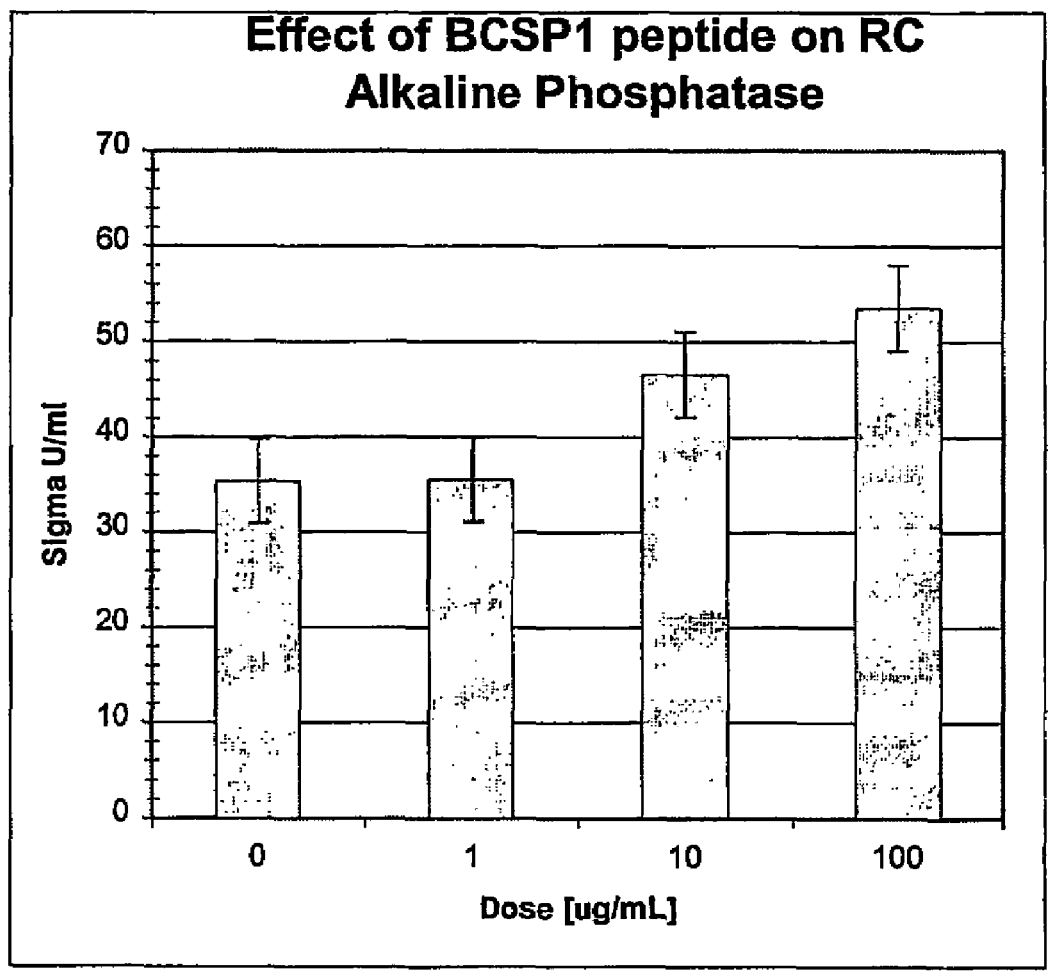
FIG. 14 shows the effects of BCSP1 on alkaline phosphatase activity in calvaria derived osteoblasts.

Cell bound alkaline phosphatase from cell lysates of rat bone marrow derived osteoblasts and rat calvaria derived osteoblasts. BCSP1 was provided at a dose range of 100 μg/ml to 1 μg/mL. Cells were cultured for 3 days prior to a 48 hr exposure to the peptide. A dose dependent response was seen from 1 μg/ml to 100 μg/ml over control (vehicle) for rat bone marrow cultures (RBM) (FIG. 13) and from 10 μg/ml to 100 μg/ml for rat calvaria cultures (RC) (FIG. 14).

Figure 15:
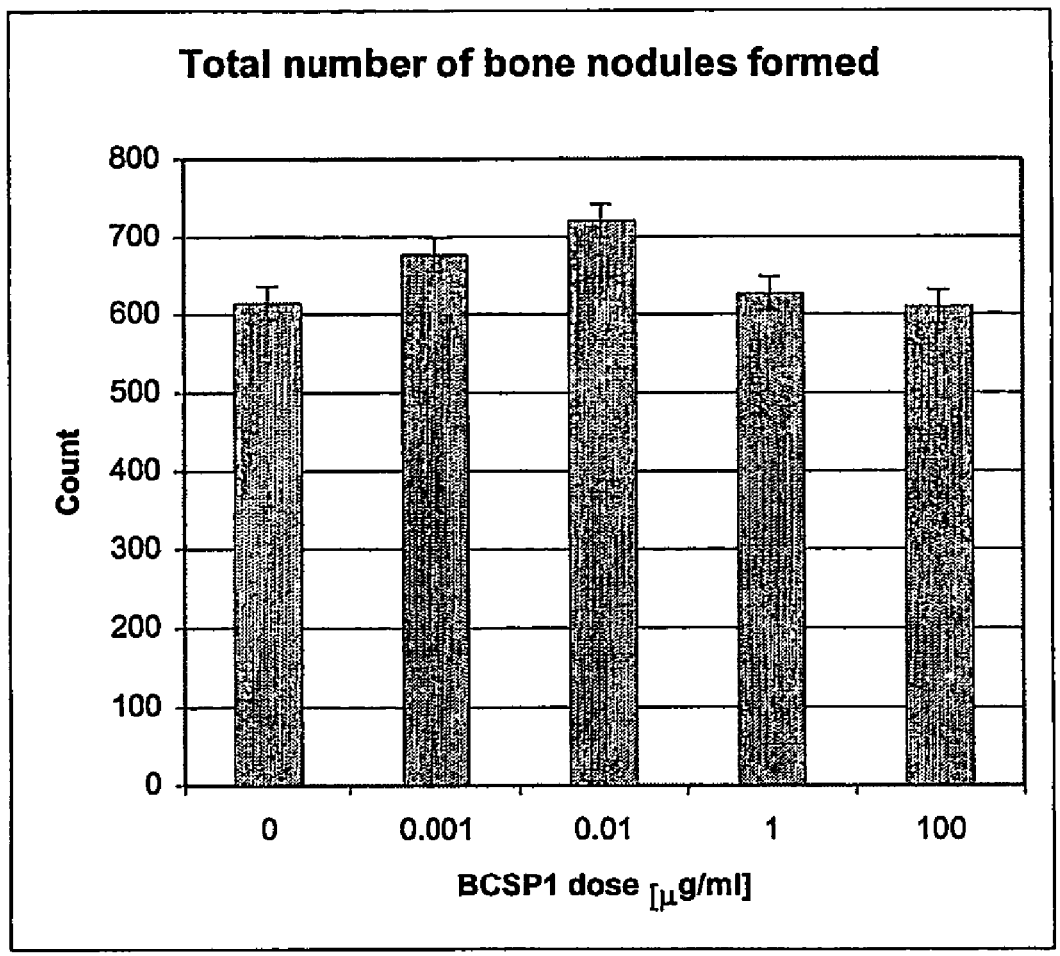
FIG. 15 shows the effects of BCSP1 on bone nodule formation in calvaria cultures.

Rat calvaria cultures were maintained for 10 days in the presence of BCSP1 at a dose range of 1 ng/ml to 100 μg/ml with dosing provided at each fluid change. Mineralized bone nodules were detected by staining with alizarin red. Image analysis was conducted with an Alpha Imager 2000™ to count and quantify nodule area. The results demonstrate minimal changes in the number of bone nodules formed with a slight increase at the 1 ng/ml and 10 ng/ml range (FIG. 15). The total mineralized bone nodule area (size of nodules) was significantly increased in the presence of BCSP1 in a dose dependent manner (FIG. 16) which was consistent with the alkaline phosphatase data. Increased alkaline phosphatase would lead to increases in total mineralized area.

Figure 16:
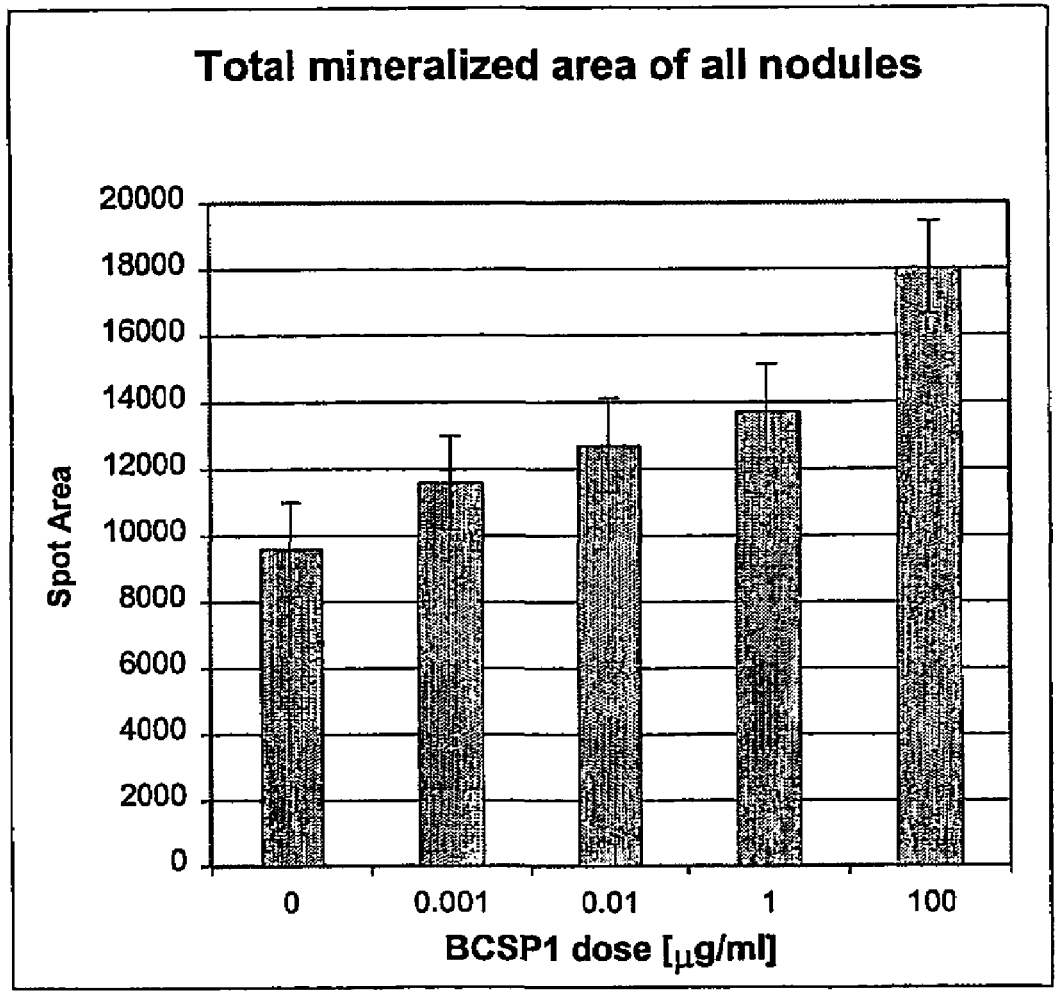
FIG. 16 shows the effects of BCSP1 on mineralization of bone nodules in calvaria cultures.

Overall the in vitro results demonstrated that BCSP1 peptide increased cell proliferation leading to an increase in alkaline phosphatase levels. Futher experimentation has demonstrated an increase in specific activity of alkaline phosphatase (not shown) suggesting a further differentiation effect due to the peptide. This is also confirmed by the increase in bone forming cells seen in the number of bone nodules formed and the total amount of mineralized area (FIG. 16).

Although preferred embodiments of the invention have been described herein in detail, it will be understood by those skilled in the art that variations may be made thereto without departing from the spirit of the invention.

The invention claimed is:

1. An isolated, bone and/or cartilage development-stimulating peptide selected from the group consisting of NGLPGPIGP* (SEQ ID NO. 1); NGLPGPIG (SEQ ID NO. 2); NGLP*GPIG (SEQ ID NO. 3); NGLP*GPIGP* (SEQ ID NO. 4); NGLPGP (SEQ ID NO. 5); PGPIG (SEQ ID NO. 7); NGLPGPIGP (SEQ ID NO. 8); PGPIGP (SEQ ID NO. 9); PGPIGPPGPR (SEQ ID NO. 10); GPIG (SEQ ID NO. 11); PGPIGPPGPRGRTGDA (SEQ ID NO. 12); GPRGRTGDA (SEQ ID NO. 13); PGPIGPP (SEQ ID NO. 14); PGPIGP* (SEQ ID NO. 15); PGPI (SEQ ID NO. 16); GLPGPIG (SEQ ID NO. 17); GPIGP* (SEQ ID NO. 18); and PIGP (SEQ ID NO. 20), wherein P is proline or hydroxyproline, and further wherein P* is hydroxyproline.

2. The peptide of claim 1, which is NGLPGPIGP* (SEQ ID NO. 1).

3. The peptide of claim 1, which is PGPIG (SEQ ID NO. 7).

4. The peptide of claim 1, wherein P is proline.

5. The peptide of claim 1, which is NGLPGPIG (SEQ ID NO. 2).

6. The peptide of claim 1, which is NGLP*GPIG (SEQ ID NO. 3).

7. The peptide of claim 1, which is NGLP*GPIGP* (SEQ ID NO. 4).

8. The peptide of claim 1, which is NGLPGP (SEQ ID NO. 5).

9. The peptide of claim 1, which is NGLPGPIGP (SEQ ID NO. 8).

10. The peptide of claim 1, which is PGPIGP (SEQ ID NO. 9).

11. The peptide of claim 1, which is PGPIGPPGPR (SEQ ID NO. 10).

12. The peptide of claim 1, which is GPIG (SEQ ID NO. 11).

13. The peptide of claim 1, which is PGPIGPPGPRGRTGDA (SEQ ID NO. 12).

14. The peptide of claim 1, which is GPRGRTGDA (SEQ ID NO. 13).

15. The peptide of claim 1, which is PGPIGPP (SEQ ID NO. 14).

16. The peptide of claim 1, which is PGPIGP* (SEQ ID NO. 15).

17. The peptide of claim 1, which is PGPI (SEQ ID NO. 16).

18. The peptide of claim 1, which is GLPGPIG (SEQ ID NO. 17).

19. The peptide of claim 1, which is GPIGP* (SEQ ID NO. 18).

20. The peptide of claim 1, which is PIGP (SEQ ID NO. 20).

21. The peptide of claim 1, wherein said peptide stimulates the activity of bone cells, bone cell precursors and cells sharing lineage therewith.

22. The peptide of claim 1, wherein said peptide stimulates the activity of cartilage cells, cartilage cell precursors and cells sharing lineage therewith.

23. The peptide of claim 1, wherein said peptide stimulates the formation of bone.

24. The peptide of claim 1, wherein said peptide stimulates the formation of cartilage.

25. The peptide of claim 1, wherein said peptide stimulates a response in vitro, ex vivo and/or in vitro.

26. The peptide of claim 1, wherein P is hydroxyproline.

27. A pharmaceutical composition comprising the peptide of claim 1 and a pharmaceutically acceptable carrier.

28. The pharmaceutical composition of claim 27, wherein said composition further comprises an agent selected from the group consisting of calcium phosphate, calcium sulfate, calcium carbonate, fibrin, hyaluronic acid, proteoglycans, calcitonin, estrogen, estradiol, prostaglandin A1, bisphosphonic acids, ipriflavones, sodium fluoride, vitamin K, bone morphogenetic proteins, fibroblast growth factor, platelet-derived growth factor, transforming growth factor, insulin-like growth factors 1 and 2, endothelin, parathyroid hormone, epidermal growth factor, leukemia inhibitory factor, osteogenin and mixtures thereof.

29. The pharmaceutical composition of claim 27, wherein said composition may be administered locally and/or systemically.

30. The pharmaceutical composition of claim 29, wherein systemic administration is selected from intravenous injection, intramuscular injection, intraperitoneal injection, oral administration, enteral administration, parenteral administration, intranasal administration, pulmonary administration, topical administration, transdermal administration and combinations thereof.

31. The peptide of claim 29, wherein local administration is provided by injection or use with an implant.

32. The peptide of claim 31, wherein said peptide is provided as a coating, filling or dispersed within a matrix of said implant.

33. The peptide of claim 32, wherein said peptide is provided with a granular or powdered biomaterial compound.

* * * * *